US009480250B2

(12) United States Patent
Kolter et al.

(10) Patent No.: US 9,480,250 B2
(45) Date of Patent: Nov. 1, 2016

(54) PRODUCTION OF SOLID SOLUTIONS OF PESTICIDES BY SHORT-TERM SUPERHEATING AND RAPID DRYING

(75) Inventors: Karl Kolter, Limburgerhof (DE); Michael Schönherr, Frankenthal (DE); Hermann Ascherl, Dirmstein (DE); Cedric Dieleman, Scheibenhard (FR); Torsten Knieriem, Mannheim (DE); Sebastian Koltzenburg, Dannstadt-Schauernheim (DE); Holger Türk, Mannheim (DE)

(73) Assignee: BASF SE, Ludwigshafen (DE)

( * ) Notice: Subject to any disclaimer, the term of this patent is extended or adjusted under 35 U.S.C. 154(b) by 678 days.

(21) Appl. No.: 12/516,376

(22) PCT Filed: Nov. 23, 2007

(86) PCT No.: PCT/EP2007/062756
§ 371 (c)(1),
(2), (4) Date: May 27, 2009

(87) PCT Pub. No.: WO2008/065051
PCT Pub. Date: Jun. 5, 2008

(65) Prior Publication Data
US 2010/0062940 A1 Mar. 11, 2010

(30) Foreign Application Priority Data
Dec. 1, 2006 (EP) ..................................... 06125227

(51) Int. Cl.
| | | |
|---|---|---|
| A01N 25/12 | (2006.01) | |
| A01P 3/00 | (2006.01) | |
| A01P 7/04 | (2006.01) | |
| A01P 13/00 | (2006.01) | |
| A01N 43/56 | (2006.01) | |
| A01N 25/10 | (2006.01) | |
| A01N 47/24 | (2006.01) | |

(52) U.S. Cl.
CPC ............... *A01N 25/12* (2013.01); *A01N 25/10* (2013.01); *A01N 47/24* (2013.01)

(58) Field of Classification Search
USPC ....................................................... 504/116
See application file for complete search history.

(56) References Cited

U.S. PATENT DOCUMENTS

| 2004/0259736 A1 | 12/2004 | Dieing et al. | |
|---|---|---|---|
| 2007/0122436 A1 | 5/2007 | Koltzenburg et al. | |
| 2008/0248117 A1* | 10/2008 | Kolter et al. | ................. 424/486 |
| 2008/0293828 A1* | 11/2008 | Bouillo et al. | ............. 514/772.3 |

FOREIGN PATENT DOCUMENTS

| CA | 2130857 | * | 3/2005 | ............. B01J 13/00 |
|---|---|---|---|---|
| CA | 25435530 | * | 5/2005 | ............. A01N 25/04 |
| CA | 2 604 496 | | 10/2006 | |
| DE | WO2006/131481 | * | 12/2006 | ............... A61K 9/14 |
| DE | WO2007/051743 | * | 5/2007 | ............... A61K 9/14 |
| JP | 2002 284608 | | 10/2002 | |
| JP | 2004 99597 | | 4/2004 | |
| WO | WO 94/23579 | | 10/1994 | |
| WO | WO99/56751 | * | 11/1999 | ........... A61K 31/445 |
| WO | WO 02/089579 | | 11/2002 | |
| WO | WO 02/090320 | | 11/2002 | |
| WO | WO 02/090321 | | 11/2002 | |
| WO | WO 03/028453 | | 4/2003 | |
| WO | WO 2004/006677 | | 1/2004 | |
| WO | WO 2004/020399 | | 3/2004 | |
| WO | WO 2005/046328 | | 5/2005 | |
| WO | WO 2006/111327 | | 10/2006 | |

OTHER PUBLICATIONS

FAO specifications and evaluations for fipronil (http://www.fao.org/fileadmin/templates/agphome/documents/Pests_Pesticides/Specs/fipronil09.pdf) date not available.*
FAO boscalid (http://web.archive.org/web/20140530222538/http://www.fao.org/fileadmin/templates/agphome/documents/Pests_Pesticides/JMPR/Evaluation06/boscalid06.pdf) Date not available.*
International Search Report completed Nov. 19, 2008, in International Application No. PCT/EP2007/062756, filed Nov. 23, 2007.
International Preliminary Report on Patentability dated Jun. 3, 2009, from corresponding International Application No. PCT/EP2007/062756, filed Nov. 23, 2007.
English language translation of the International Preliminary Report on Patentability dated Jun. 3, 2009, from corresponding International Application No. PCT/EP2007/062756, filed Nov. 23, 2007.

* cited by examiner

*Primary Examiner* — Mina Haghighatian
*Assistant Examiner* — Erin Hirt
(74) *Attorney, Agent, or Firm* — Brinks Gilson & Lione

(57) ABSTRACT

The present invention relates to a method for the production of solid solutions of sparingly soluble pesticides, pulverulent products that are obtained by said method and their use for pesticide formulations.

12 Claims, 2 Drawing Sheets

PRODUCTION OF SOLID SOLUTIONS OF PESTICIDES BY SHORT-TERM SUPERHEATING AND RAPID DRYING

CROSS-REFERENCE TO RELATED APPLICATIONS

This application is a National Stage application of International Application No. PCT/EP2007/062756 filed Nov. 23, 2007, the entire contents of which is hereby incorporated herein by reference. This application also claims the benefit under 35 U.S.C. §119 of European Patent Application No. 06125227.6 filed Dec. 1, 2006, the entire contents of which is hereby incorporated herein by reference.

BACKGROUND OF THE INVENTION

The present invention relates to a method for the production of solid solutions of sparingly soluble pesticides, pulverulent products that are obtained by said method and use thereof for pesticide formulations.

Pesticides that are sparingly soluble in aqueous media present difficulties during formulation, because with active substances of this kind it is not easy to develop formulations in which the pesticide is bioavailable. One approach is to form solid solutions, in which the pesticide is incorporated in molecularly disperse form, often with the result that much higher bioavailability is achieved.

The term solid solution is often used incorrectly in the literature, as materials with embedded solid crystalline substances are often called solid solutions. Strictly speaking, these are solid dispersions. In this text, solid solution means a true molecularly disperse distribution.

To date, the production of these solid solutions has been a very expensive process.

The following methods are currently available:
1. Melting of active substance and polymer at high temperature and extrusion (see for example WO 03/028453). This method has the disadvantage that high temperatures act on the active substance for some minutes and in addition large molded bodies are formed, requiring laborious comminution by grinding, to be made suitable for granulation or tableting. Furthermore, during melt extrusion, in addition to thermal loading there is also the action of shearing forces, which can lead to decomposition of the active substances.
2. Dissolution of active substance and polymer in an organic solvent, which dissolves both, and evaporation of the solvent or spray drying, alternatively dissolution of the active substance in an organic, water-miscible solvent and dissolution of the polymer in water (see for example WO 05/046328). This method has in itself the disadvantage that it requires extensive use of organic solvents, which are harmful to the environment and pose an explosion hazard, and appreciable costs are incurred when they are used.
3. Dispersion of active substance in an aqueous polymer solution, for example by wet grinding and spray drying. In this case, if the active substance is not water-soluble, solid solutions are not formed, only solid dispersions, which certainly do not have the same properties as molecularly disperse solutions, particularly with respect to bioavailability.

BRIEF SUMMARY OF THE INVENTION

The aim of the present invention was therefore to find a method that avoids organic solvents, does not involve significant thermal stress on the pesticides and results directly in a product with good formulation properties and flowability.

Another aim of the present invention was to provide formulations in the form of solid solutions, which have
  high bioavailability and/or
  good shelf life; and/or
  a content of active substance that is as high as possible.

Accordingly, a method was found for the production of pulverulent solid solutions of sparingly soluble pesticides, in which the sparingly soluble pesticide is molecularly dispersed in a matrix of inactive ingredients, by spraying a solution of the sparingly soluble pesticide and of the inactive ingredients of the matrix, wherein an aqueous suspension of the sparingly soluble pesticide is heated in the presence of the inactive ingredients of the matrix at pressures from 0.08 to 20 MPa to temperatures >80° C. to 20 350° C., preferably 90° C. to 350° C. and the sparingly soluble pesticide is dissolved, and then by spraying and drying is converted to pulverulent form, with the temperature of the spray solution at feed into the spraying device being 80° C. to 300° C., preferably 90° C. to 250° C.

DETAILED DESCRIPTION OF THE INVENTION

Figure 1:
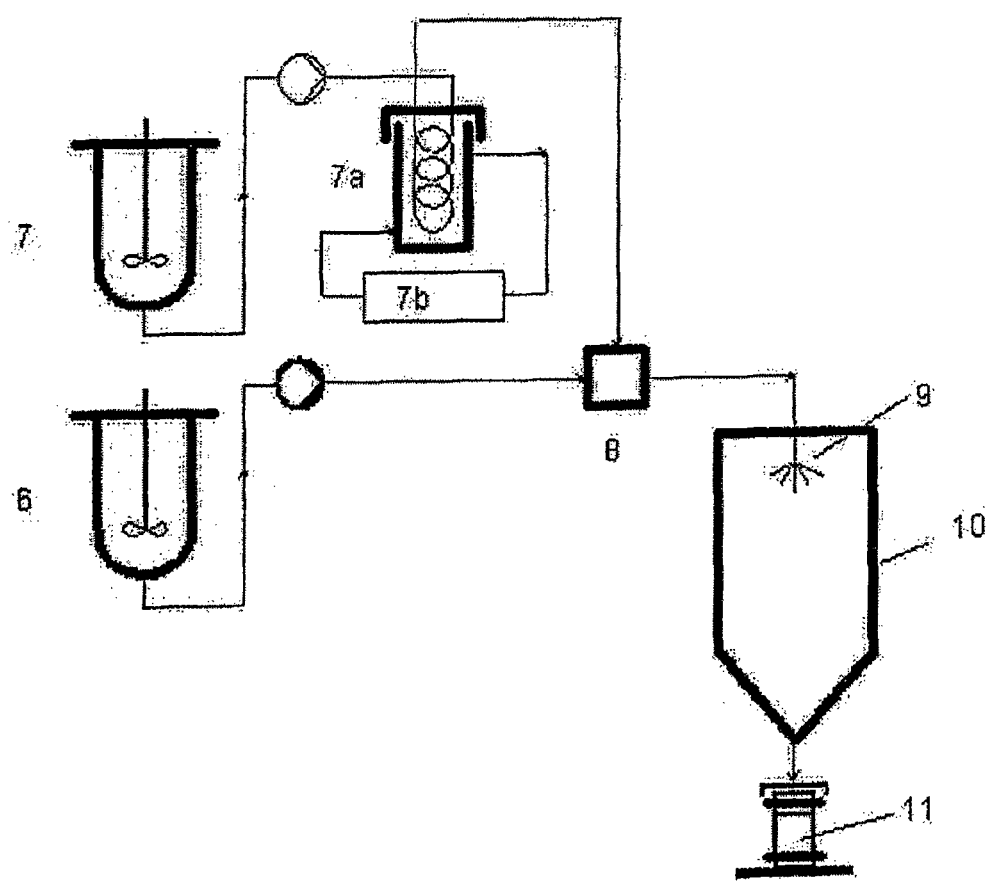
FIG. 1 illustrates a procedure for use with an embodiment of the present invention.
Figure 2:
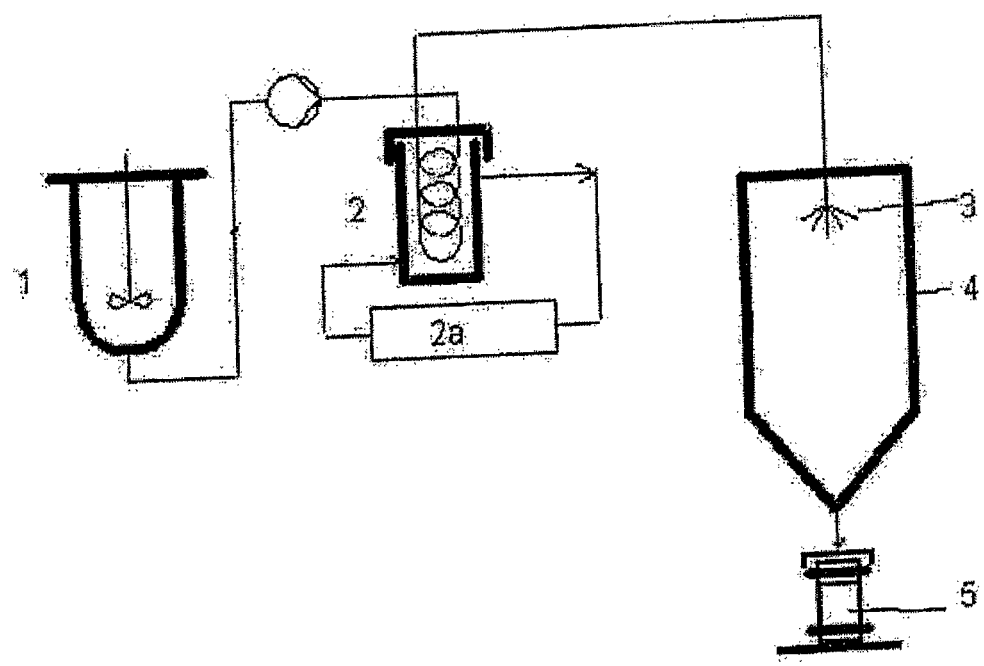
FIG. 2 illustrates a procedure for use with an alternative embodiment of the present invention.

Solid solution means, according to the invention, a state in which the active substance (i.e. the pesticide) is distributed as a molecular dispersion in a matrix of inactive ingredients. In this state, crystalline fractions of the active substance can no longer be detected by X-ray diffractometry. As the limit of detection for crystalline fractions in X-ray diffractometry is 3 wt. %, the expression "no crystalline fractions" means that less than 3 wt. % of crystalline fractions is present. The state of molecularly disperse distribution can be determined using the method of differential scanning calorimetry (DSC). With a molecularly disperse distribution, a melting peak is no longer observed in the region of the melting point of the active substance. The limit of detection of this method is 1 wt. %.

"Sparingly soluble pesticide substances" means, in the sense of the invention, substances whose saturation solubility at room temperature (20° C.) in at least one of the following media is less than 1 wt. %: water, 0.1-molar aqueous hydrochloric acid, aqueous phosphate buffer pH 7.2, 0.9 wt. % aqueous sodium chloride solution.

Here, the term pesticide means at least one active substance selected from the group comprising the insecticides, fungicides, herbicides and/or safeners (see Pesticide Manual, 13th ed. (2003)). Combinations of two or more of the active substances stated below can also be used.

The following list of sparingly soluble insecticides shows possible active substances, but is not to be restricted to these:
A.1. Organo(thio) phosphates: azinphos-methyl, chlorpyrifos, chlorpyrifos-methyl, chlorfenvinphos, diazinon, disulfoton, ethion, fenitrothion, fenthion, isoxathion, malathion, methidathion, methyl-parathion, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

A.2. Carbamates: alanycarb, bendiocarb, benfuracarb, carbaryl, carbofuran, carbosulfan, fenoxycarb, furathiocarb, methiocarb, methomyl, oxamyl, pirimicarb, thiodicarb, triazamate;

A.3. Pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin;

A.4. Growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, a tetronic acid derivative of formula $\Gamma^1$, ($\Gamma^1$)

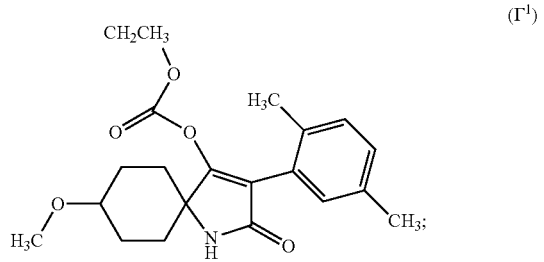 [SMILES: CCOC(=O)OC1=C(c2cc(C)ccc2C)C(=O)NC12CCC(OC)CC2]

A.5. Nicotine receptor agonists/antagonists: clothianidin, dinotefuran, thiacloprid;

A.6. GABA antagonists: acetoprole, endosulfan, ethiprole, fipronil, vaniliprole;

A.7. Macrolide insecticides: abamectin, emamectin, milbemectin, lepimectin, spinosad;

A.8. METI I acaricides: fenazaquin, pyridaben, tebufenpyrad, tolfenpyrad;

A.9. METI II and III compounds: acequinocyl, fluacyprim, hydramethylnon;

A.10. Uncoupler compounds: chlorfenapyr;

A.11. Inhibitors of oxidative phosphorylation: cyhexatin, diafenthiuron, fenbutatin oxide, propargite;

A.12. Compounds that interfere with molting: cryomazine;

A.13. Inhibitors of mixed function oxidase: piperonyl butoxide;

A.14. Sodium channel blockers: indoxacarb, metaflumizone;

A.15. Miscellaneous: benclothiaz, bifenazate, flonicamide, pyridalyl, pymetrozine, sulfur, thiocyclam and aminoisothiazole compounds of formula $\Gamma^2$,

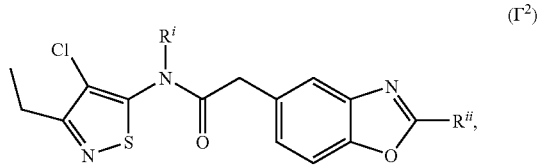

where $R^i$ stands for $-CH_2OCH_2CH_3$ or H and $R^{ii}$ stands for $CF_2CF_2CF_3$ or $CH_2CH(CH_3)_3$, anthranilamide compounds of formula $\Gamma^3$,

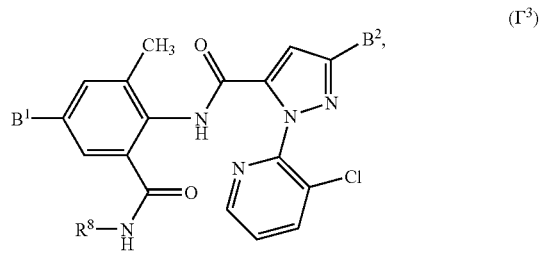

where $B^1$ stands for hydrogen or chlorine, B2 for bromine or $CF_3$, and RB for $CH_3$ or $CH(CH_3)_2$, and malononitrile compounds as described in JP 2002 284608, WO 02/89579, WO 02/90320, WO 02/90321, WO 04/06677, WO 04/20399, or JP 2004 99597, N—R'-2,2-dihalo-1-R"cyclopropanecarboxamide-2-(2,6-dichloro-α,α,α,α-tri-fluoro-p-tolyl)hydrazone or N—R'-2,2-di(R''')propionamide-2-(2,6-dichloro-α,α,α,α-trifluoro-p-tolyl)-hydrazone, in which R' stands for methyl or ethyl, halo stands for chlorine or bromine, R" stands for hydrogen or methyl and R''' stands for methyl or ethyl.

The following list of sparingly soluble fungicides shows possible active substances, but is not to be restricted to these:

1. Strobilurins

Azoxystrobin, dimoxystrobin, enestroburin, fluoxastrobin, kresoxim-methyl, metominostrobin, picoxystrobin, pyraclostrobin, trifloxystrobin, orysastrobin, (2-chloro-[1-(3-methyl-benzyloxyimino)-ethyl]-benzylmethyl carbamate, (2-chloro-5-[1-(6-methyl-pyridin-2-ylmethoxyimino)-ethyl]-benzyl)-methyl carbamate, 2-(ortho-((2,5-dimethylphenyl-oxymethylene)phenyl)-3-methoxy-methyl acrylate;

2. Carboxylic Acid Amides

Carboxylic acid anilides: benalaxyl, benodanil, boscalid, carboxin, mepronil, fenfuram, fenhexamide, flutolanil, furametpyr, metalaxyl, ofurace, oxadixyl, oxycarboxin, penthiopyrad, thifluzamide, tiadinil, 4-difluoromethyl-2-methyl-thiazole-5-carboxylic acid-(4'-bromo-biphenyl-2-yl)amide, 4-difluoromethyl-2-methyl-thiazole-5-carboxylic acid-(4'-trifluoromethyl-biphenyl-2-yl) amide, 4-difluoromethyl-2-methyl-thiazole-5-carboxylic acid-(4'-chloro-3'-fluoro-biphenyl-2-yl)-amide, 3-difluoromethyl-1-methyl-pyrazole-4-carboxylic acid-(3',4'-dichloro-4-fluoro-biphenyl-2-yl)-amide, 3,4-dichloro-isothiazole-5-carboxylic acid-(2-cyanophenyl)amide;

3-difluoromethyl-1-methyl-pyrazole-4-carboxylic acid-(3',4'-dichloro-5-fluoro-biphenyl-2-yl)amide, 3-difluoromethyl-1-methyl-1H-pyrazole-4-carboxylic acid-(2-bicyclopropyl-2-ylphenyl)amide)

Carboxylic acid morpholides: dimethomorph, flumorph;
Benzoic acid amides: flumetover, fluopicolide (picobenzamid), zoxamide;
Other carboxylic acid amides: carpropamid, diclocymet, mandipropamid, N-(2-(4-[3-(4-chloro-phenyl)-prop-2-ynyloxy]-3-methoxy-phenyl)-ethyl)-2-methanesulfonylamino-3-methyl-butyramide, N-(2-(4-[3-(4-chloro-phenyl)-prop-2-ynyloxy]-3-methoxy-phenyl)ethyl)-2-ethanesulfonylamino-3-methyl-butyramide, 3-difluoromethyl-1-methyl-pyrazole-4-carboxylic acid-(3',4'-dichloro-5-fluoro-biphenyl-2-yl)-amide and 3-difluoromethyl-1-methyl-1H-pyrazole-4-carboxylic acid-(2-bicyclopropyl-2-yl-phenyl)amide);

1-Methylpyrazole-4-yl-carboxylic acid anilides: 3-trifluoromethyl-1-methyl-1H-pyrazole-4-carboxylic acid-N-(2'-fluoro-4'-chloro-5'-methoxybiphenyl-2-yl)-amide, 3-trifluoromethyl-1-methyl-1H-pyrazole-4-carboxylic acid-N-(2'-fluoro-4'-chloro-5'-methylbiphenyl-2-yl)-amide, 3-trifluoromethyl-1-methyl-1H-pyrazole-4-carboxylic acid-N-(3',4',5'-trifluorobiphenyl-2-yl)amide, 3-trifluoromethyl-1-methyl-1H-pyrazole-4-carboxylic acid-N-(2',4',5'-trifluorobiphenyl-2-yl)-amide, 3-difluoromethyl-1-methyl-1H-pyrazole-4-carboxylic acid-N-(2'-fluoro-4'-chloro-5'-methoxybiphenyl-2-yl)-amide, 3-trifluoromethyl-1-methyl-1H-pyrazole-4-carboxylic acid-N-(2',3',4'-trifluorobiphenyl-2-yl)-amide, 3-difluoromethyl-1-methyl-1H-pyrazole-4-carboxylic acid-N-(2'-fluoro-4'-chloro-5'-methylbiphenyl-2-yl)-amide, 3-difluoromethyl-1-methyl-1H-pyrazole-4-carboxylic acid-N-(3',4',5'-trifluorobiphenyl-2-yl)amide, 3-difluoromethyl-1-methyl-1H-pyrazole-4-carboxylic acid-N-(2',4',5'-trifluorobiphenyl-2-yl)-amide, 3-fluoromethyl-1-methyl-1H-pyrazole-4-carboxylic acid-N-(3',4',5'-trifluorobiphenyl-2-yl)-amide, 3-chlorodifluoromethyl-1-methyl-1H-pyrazole-4-carboxylic acid-N-(3',4',5'-trifluorobiphenyl-2-yl)-amide, 3-chlorofluoromethyl-1-methyl-1H-pyrazole-4-carboxylic acid-N-(3',4',5'-trifluorobiphenyl-2-yl)-amide, 3-fluoromethyl-1-methyl-1H-pyrazole-4-carboxylic acid-N-(2',3',4'-trifluorobiphenyl-2-yl)-amide and 3-fluoromethyl-1-methyl-1H-pyrazole-4-carboxylic acid-N-(2',4',5'-trifluorobiphenyl-2-yl)-amide.

3. Azoles

Triazoles: bitertanol, bromuconazole, cyproconazole, difenoconazole, diniconazole, enilconazole, epoxiconazole, fenbuconazole, flusilazole, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole;

Imidazoles: cyazofamid, imazalil, pefurazoate, prochloraz, triflumizole;

Benzimidazoles: benomyl, carbendazim, fuberidazole, thiabendazole;

Miscellaneous: ethaboxam, etridiazole, hymexazole;

4. Nitrogen-Containing Heterocyclyl Compounds:

Pyridines: fluazinam, pyrifenox, 3-[5-(4-chloro-phenyl)-2,3-dimethyl-isoxazolidine-3-yl]pyridine;

Pyrimidines: bupirimate, cyprodinil, ferimzone, fenarimol, mepanipyrim, nuarimol, pyrimethanil;

Piperazines: triforine;

Pyrroles: fludioxonil, fenpiclonil;

Morpholines: aldimorph, dodemorph, fenpropimorph, tridemorph;

Dicarboximides: iprodione, procymidone, vinclozolin;

Miscellaneous: acibenzolar-S-methyl, anilazin, captan, captafol, dazomet, diclomezine, fenoxanil, folpet, fenpropidin, famoxadone, fenamidone, octhilinone, probenazole, proquinazid, quinoxyfen, tricyclazole, 5-chloro-7-(4-methyl-piperidine-1-yl)-6-(2,4,6-trifluoro-phenyl)-[1,2,4]triazolo[1,5-a]pyrimidine, 2-butoxy-6-iodo-3-propyl-chromen-4-one, 3-(3-bromo-6-fluoro-2-methyl-indole-1-sulfonyl)-[1,2,4]triazole-1-sulfonic acid dimethylamide;

5. Carbamates and Dithiocarbamates

Carbamates: diethofencarb, flubenthiavalicarb, iprovalicarb, propamocarb, 3-(4-chloro-phenyl)-3-(2-isopropoxycarbonylamino-3-methyl-butyrylamino)-propionic acid methyl ester, N-(1-(1-(4-cyanophenyl)ethanesulfonyl)-but-2-yl) carbaminic acid-(4-fluorophenyl)ester;

6. Miscellaneous Fungicides

Organometallic compounds: fentin salts;

Sulfur-containing heterocyclyl compounds: isoprothiolane, dithianon;

Organophosphorus compounds: edifenphos, fosetyl, fosetyl-aluminum, iprobenfos, pyrazophos, tolclofos-methyl, phosphoric acid and salts thereof;

Organochlorine compounds: thiophanate methyl, chlorothalonil, dichlofluanid, tolylfluanid, flusulfamide, phthalide, hexachlorobenzene, pencycuron, quintozene;

Nitrophenyl derivatives: binapacryl, dinocap, dinobuton;

Miscellaneous: spiroxamine, cyflufenamid, cymoxanil, metrafenone.

The following list of sparingly soluble herbicides shows possible active substances, but is not to be restricted to these:

Compounds that inhibit lipid biosynthesis, e.g. chlorazifop, clodinafop, clofop, cyhalofop, cyclofop, fenoxaprop, fenoxaprop-p, fenthiaprop, fluazifop, fluazifop-P, haloxyfop, haloxyfop-P, isoxapyrifop, metamifop, propaquizafop, quizalofop, quizalofop-P, trifop, or their esters, butroxydim, cycloxydim, profoxydim, sethoxydim, tepraloxydim, tralkoxydim, butylate, cycloat, diallat, dimepiperat, EPTC, esprocarb, ethiolate, isopolinate, methiobencarb, molinate, orbencarb, pebulate, prosulfocarb, sulfallat, thiobencarb, thiocarbazil, triallat, vernolat, benfuresat, ethofumesat and bensulid;

ALS inhibitors such as amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac; provided the pH value is <8 compounds that inhibit photosynthesis, such as atraton, atrazine, ametryne, aziprotryne, cyanazine, cyanatryne, chlorazine, cyprazine, desmetryne, dimethametryne, dipropetryne, eglinazine, ipazine, mesoprazine, methometon, methoprotryne, procyazine, proglinazine, prometon, prometryne, propazine, sebuthylazine, secbumeton, simazine, simeton, symmetryne, terbumeton, terbuthylazine and terbutryne;

Protoporphyrinogenic IX oxidase inhibitors such as acifluorfen, bifenox, chlomethoxyfen, chlornitrofen, ethoxyfen, fluorodifen, fluoroglycofen, fluoronitrofen, fomesafen, furyloxyfen, halosafen, lactofen, nitrofen, nitrofluorfen, oxyfluorfen, fluazolate, pyraflufen, cinidon-ethyl, flumiclorac, flumioxazin, flumipropyn, fluthiacet, thidiazimin, oxadiazon, oxadiargyl, azafenidin, carfentrazone, sulfentrazone, pentoxazone, benzfendizone, butafenacil, pyraclonil, profluazol, flufenpyr, flupropacil, nipyraclofen and etnipromid;

Herbicides such as metflurazon, norflurazon, flufenican, diflufenican, picolinafen, beflubutamid, fluridone, flurochloridone, flurtamone, mesotrione, sulcotrione, isoxachlortole, isoxaflutole, benzofenap, pyrazolynate, pyrazoxyfen, benzobicyclon, amitrole, clomazone, aclonifen, 4-(3-trifluoromethylphenoxy)-2-(4-trifluoromethylphenyl)pyrimidine, and 3-heterocyclyl-substituted benzoyl derivatives of formula (cf. WO-A-96/26202, WO-A-97/41116, WO-A-97/41117 and WO-A-97/41118)

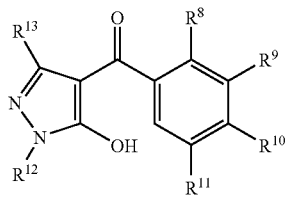

in which the substituents $R^8$ to $R^{13}$ have the following meaning:
$R^8$, $R^{10}$ hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl or $C_1$-$C_6$-alkylsulfonyl;
$R^9$ denotes a heterocyclic radical from the group comprising thiazol-2-yl, thiazol-4-yl, thiazol-5-yl, isoxazol-3-yl, isoxazol-4-yl, isoxazol-5-yl, 4,5-dihydroisoxazol-3-yl, 4,5-dihydroisoxazol-4-yl and 4,5-dihydroisoxazol-5-yl, in which the stated radicals can carry one or more substituents e.g. can be mono-, di-, tri- or tetra-substituted with halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio;
$R^{11}$=hydrogen, halogen or $C_1$-$C_6$-alkyl;
$R^{12}$=$C_1$-$C_6$-alkyl;
$R^{13}$=hydrogen or $C_1$-$C_6$-alkyl,
provided the pH value <8.

Mitosis inhibitors such as benfluralin, butralin, dinitramine, ethalfluralin, fluchloralin, isopropalin, methalpropalin, nitralin, oryzalin, pendimethalin, prodiamine, profluralin, trifluralin, amiprofos-methyl, butamifos, dithiopyr, thiazopyr, propyzamide, chlorthal, carbetamide, chlorpropham and propham;

VLCFA inhibitors such as acetochlor, alachlor, butachlor, butenachlor, delachlor, diethatyl, dimethachlor, dimethenamide, dimethenamide-P, metazachlor, metolachlor, S-metolachlor, pretilachlor, propisochlor, prynachlor, terbuchlor, thenylchlor, xylachlor, CDEA, epronaz, diphenamide, napropamides, naproanilide, pethoxamide, flufenacet, mefenacet, fentrazamide, anilofos, piperophos, cafenstrole, indanofan and tridiphan;

Inhibitors for the biosynthesis of cellulose such as dichlobenil, chlorthiamide, isoxaben and flupoxam;

Herbicides such as dinofenat, dinoprop, dinosam, dinoseb, dinoterb, DNOC, etinofen and medinoterb;
in addition: benzoylprop, flamprop, flamprop-M, bromobutide, chlorflurenol, cinmethylin, methyldymron, etobenzanide, pyributicarb, oxaziclomefone, triaziflam and methyl bromide.

The following list shows possible sparingly soluble safeners, but is not to be restricted to these:
benoxacor, cloquintocet, cyometrinil, dicyclonone, dietholate, fenchlorazole, fenclorim, flurazole, fluxofenim, furilazole, isoxadifen, mefenpyr, mephenate, naphthalic anhydride, 2,2,5-trimethyl-3-(dichloroacetyl)-1,3-oxazolidine (R-29148), 4-(dichloroacetyl)-1-oxa-4-azaspiro[4.5]decane (AD-67; MON 4660) and oxabetrinil.

Preferred fungicides are triazoles such as bitertanol, bromuconazole, cyproconazole, difenoconazole, diniconazole, enilconazole, epoxiconazole, fenbuconazole, flusilazole, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole, strobilurines such as azoxystrobin, dimoxystrobin, enestroburin, fluoxastrobin, kresoxim-methyl, metominostrobin, picoxystrobin, pyraclostrobin, trifloxystrobin, orysastrobin, (2-chloro-5-[1-(3-methyl-benzyloxyimino)-ethyl]-benzyl) methyl carbamate, (2-chloro-5-[1-(6-methyl-pyridine-2-yl-methoxyimino)-ethyl]benzyl)-methyl carbamate, 2-(ortho-((2,5-dimethylphenyl-oxymethylene)phenyl)-3-methoxy-methyl acrylate and 5-chloro-7-(4-methylpiperidine-1-yl)-6-(2,4,6-trifluoro-phenyl)-[1,2,4]triazolo[1,5-a]pyrimidine and boscalid. In another preferred embodiment, 1-methyl-pyrazole-4-yl-carboxylic acid anilides are preferred.

Quite especially preferred fungicides are epoxiconazole, metconazole, pyraclostrobin, kresoxim-methyl and 5-chloro-7-(4-methyl-piperidine-1-yl)-6-(2,4,6-trifluoro-phenyl)-[1,2,4]triazolo[1,5-a]pyrimidine and boscalid. In another quite especially preferred embodiment 3-trifluoromethyl-1-methyl-1H-pyrazole-4-carboxylic acid-N-(2'-fluoro-4'-chloro-5'-methoxybiphenyl-2-yl)-amide, 3-trifluoromethyl-1-methyl-1H-pyrazole-4-carboxylic acid-N-(2'-fluoro-4'-chloro-5'-methylbiphenyl-2-yl)-amide, 3-trifluoromethyl-1-methyl-1H-pyrazole-4-carboxylic acid-N-(3',4',5'-trifluorobiphenyl-2-yl)-amide, 3-trifluoromethyl-1-methyl-1H-pyrazole-4-carboxylic acid-N-(2',4',5'-trifluorobiphenyl-2-yl)-amide, 3-difluoromethyl-1-methyl-1H-pyrazole-4-carboxylic acid-N-(2'-fluoro-4'-chloro-5'-methoxybiphenyl-2-yl)-amide, 3-trifluoromethyl-1-methyl-1H-pyrazole-4-carboxylic acid-N-(2',3',4'-trifluorobiphenyl-2-yl)-amide, 3-difluoromethyl-1-methyl-1H-pyrazole-4-carboxylic acid-N-(2'-fluoro-4'-chloro-5'-methylbiphenyl-2-yl)-amide, 3-difluoromethyl-1-methyl-1H-pyrazole-4-carboxylic acid-N-(3',4',5'-trifluorobiphenyl-2-yl)-amide, 3-difluoromethyl-1-methyl-1H-pyrazole-4-carboxylic acid-N-(2',4',5'-trifluorobiphenyl-2-yl)-amide, 3-fluoromethyl-1-methyl-1H-pyrazole-4-carboxylic acid-N-(3',4',5'-trifluorobiphenyl-2-yl)-amide, 3-chlorodifluoromethyl-1-methyl-1H-pyrazole-4-carboxylic acid-N-(3',4',5'-trifluorobiphenyl-2-yl)-amide, 3-chlorofluoromethyl-1-methyl-1H-pyrazole-4-carboxylic acid-N-(3',4',5'-trifluorobiphenyl-2-yl)-amide, 3-fluoromethyl-1-methyl-1H-pyrazole-4-carboxylic acid-N-(2',3',4'-trifluorobiphenyl-2-yl)-amide and 3-fluoromethyl-1-methyl-1H-pyrazole-4-carboxylic acid-N-(2',4',5'-trifluorobiphenyl-2-yl)amide are preferred.

In another preferred embodiment, mixtures of fungicides are preferred that include at least one azole. Mixtures comprising epoxiconazole and metconazole; and mixtures comprising at least one azole and at least one strobilurin, in particular epoxiconazole and pyraclostrobin, are preferred.

In another preferred embodiment, mixtures of fungicides are preferred that include at least one 1-methylpyrazole-4-ylcarboxylic acid anilide. Mixtures of at least one 1-methylpyrazole-4-yl-carboxylic acid anilide and at least one azole, with one azole preferably being metconazole or epoxiconazole; or
at least one 1-methylpyrazole-4-yl-carboxylic acid anilide and at least one strobilurin, with one strobilurin preferably being pyraclostrobin; or at least one 1-methylpyrazole-4-yl-carboxylic acid anilide, at least one azole and at least one strobilurin, with one azole preferably being metconazole or epoxiconazole; and with one strobilurin preferably being pyraclostrobin, are preferred.

Preferred insecticides are metaflumizon, fipronil and alpha-cypermethrin.

The solid solutions produced by the method according to the invention can have the following quantitative composition:
(i) 1 to 50 wt. % of at least one sparingly soluble pesticide,
(ii) 10 to 99 wt. % of at least one water-soluble inactive ingredient of the matrix
(iii) 0 to 30 wt. % of one or more surfactants/solubilizers,
(iv) 0 to 50 wt. % of other inactive ingredients,
with the amounts of the components (i) to (v) adding up to 100 wt. %.

The expression at least one sparingly soluble pesticide means that one, two or more pesticides can be used. Preferably one or two pesticides are used.

Basically all substances that are able to form solid solutions with active substances are suitable as matrix-forming inactive ingredients.

For example, water-soluble polymers from the following structural classes are suitable polyvinylpyrrolidone, vinylpyrrolidone-vinylacetate copolymers, polyvinylcaprolactams, polyvinylformamide, polyvinylacetamide, polyacrylates, polymethacrylates, polyacrylamides, polyethylene-imines, polyvinylamines, hydroxyalkylcelluloses, alkylhydroxyalkylcelluloses, carboxyalkylcelluloses, alkylhydroxyalkylcellulose-acetate-succinates, alkyl-hydroxy-alkylcellulose-acetate-phthalates, alkylhydroxyalkylcellulose-phthalates, celluloseacetate-phthalates, starches, hydroxyalkylstarches, carboxyalkylstarches, modified starch, octenylsuccinate-starches, dextrans, polyoxyethylene-polyoxypropylene block copolymers, polyethylene oxides, polypropylene oxides, and polyamino acids.

Polymer compositions are also suitable as matrix-forming inactive ingredients such as are described in WO06/084680, which can be obtained by reaction of
a) at least one polymer P1*, which has functional groups R1 that are reactive to isocyanate groups and is made up of ethylenically unsaturated monomers M1, with the monomers M1* containing more than 20 wt. %, relative to the total amount of monomers M1*, of monomers M1*a, which have at least one functional group FG, which is selected from tertiary amino groups, imino groups, carboxyamide groups, nitrile groups, lactam groups, keto groups, aldehyde groups, urea groups, polyether groups, carboxyl groups, sulfonyl groups, hydroxysulfonyl groups and sulfonamide groups,
b) at least one poly-$C_2$-$C_4$-alkylene ether P2*, which has functional groups R2 that are reactive to isocyanate groups,
c) with at least one compound V, containing isocyanate groups, and having a functionality of at least 1.5 with respect to the isocyanate groups.

The term "functionality", here and hereinafter, stands for the average number of the particular functional groups R1 or R2 per molecule or per polymer chain.

As polymers P1*, consideration may be given basically to all polymers made up of ethylenically unsaturated monomers M1*, which have the required number of reactive groups R1 and whose constituent monomers M1*comprise more than 20 wt. %, in particular at least 25 wt. %, especially preferably at least 30 wt. % and quite especially preferably at least 35 wt. % of functionalized monomers M1*a. The proportion of monomers M1*a in the monomers M1* can be up to 100 wt. % and is advantageously in the range from 25 to 90 wt. %, in particular in the range from 30 to 80 wt. %, especially preferably in the range from 30 to 70 wt. % and quite especially preferably in the range from 35 to 60 wt. %.

The monomers M1*a possess, in addition to the ethylenically unsaturated double bond, one or more, e.g. one or two functional groups FG. As a rule this endows the monomers M1*a with increased water solubility. The water solubility of the monomers M1*a is therefore often at least 50 g/l and in particular at least 80 g/l at 25° C. and 1013 mbar.

The monomers M1*a can be both acidic or anionic, and basic or neutral.

In a first preferred embodiment the monomers M1*a essentially comprise only neutral monomers M1*a.

In a second preferred embodiment the monomers M1*a essentially comprise only basic monomers M1*a.

In a third preferred embodiment the monomers M1*a essentially comprise only acidic monomers M1*a.

In a fourth preferred embodiment the monomers M1*a essentially comprise a mixture of neutral and basic monomers M1*a. In this embodiment the weight ratio of neutral to basic monomers is preferably in the range from 1:10 to 10:1 and in particular in the range from 5:1 to 1:2.

In a fifth preferred embodiment the monomers M1*a essentially comprise a mixture of neutral and acidic monomers M1*a. In this embodiment the weight ratio of neutral to acidic monomers is preferably in the range from 1:10 to 10:1 and in particular in the range from 5:1 to 1:2.

Among the embodiments 1 to 5, the embodiments 1, 2 and 4 are especially preferred.

"Essentially" means here at least 90 wt. %, and in particular at least 95 wt. %, based on the weight of the monomers M1*a.

The neutral monomers M1*a include for example
amides and $C_1$-$C_4$-alkyloxyalkylamides of monoethylenically unsaturated $C_3$-$C_8$-monocarboxylic acids such as acrylamide, methacrylamide, N-(methoxymethyl)(meth)acrylamide, N-(ethoxymethyl)(meth)acrylamide, N-(2-methoxyethyl)(meth)acrylamide, N-(2-ethoxyethyl)(meth)acrylamide and the like;
monoethylenically unsaturated nitriles such as acrylonitrile and methacrylonitrile;
N-vinylamides of aliphatic, cycloaliphatic or aromatic carboxylic acids, in particular
N-vinylamides of aliphatic carboxylic acids with 1 to 4 carbon atoms such as N-vinylformamide, N-vinylacetamide, N-vinylpropionic acid amide and N-vinylbutyramide;
N-vinyllactams with 5 to 7 ring atoms, e.g. N-vinylpyrrolidone, N-vinylpiperidone, N-vinylmorpholinone and N-vinylcaprolactam;
monoethylenically unsaturated monomers bearing urea groups such as
N-vinyl- and N-allylurea and derivatives of imidazolidin-2-one, e.g.
N-vinyl- and N-allylimidazolidin-2-one,
N-vinyloxyethylimidazolidin-2-one,
N-allyloxyethylimidazolidin-2-one,
N-(2-acrylamidoethyl)imidazolidin-2-one,
N-(2-acryloxyethyl)imidazolidin-2-one,
N-(2-methacrylamidoethyl)imidazolidin-2-one,
N-(2-methacryloxyethyl)imidazolidin-2-one (=ureidomethacrylate),
N-[2-(acryloxyacetamido)ethyl]imidazolidin-2-one,
N-[2-(2-acryloxyacetamido)ethyl]imidazolidin-2-one,
N-[2-(2-methacryloxyacetamido)ethyl]imidazolidin-2-one;
monoethylenically unsaturated monomers having aldehyde or keto groups such as 3-(acrylamido)-3-methylbutane-2-one (diacetone acrylamide), 3-(methacrylamido)-3-methylbutane-2-one, 2,4-dioxapentyl acrylate and 2,4-dioxapentylmethacrylate.

Preferred neutral monomers are N-vinyllactams, in particular N-vinylpyrrolidone and monomers bearing urea groups, in particular N-(2-acrylamidoethyl)imidazolin-2-one and N-(2-methacrylamidoethyl)-imidazolin-2-one.

The basic monomers M1*a include for example
vinyl-substituted nitrogen heteroaromatics such as 2-, 3- and 4-vinylpyridine, N-vinylimidazole; and
monoethylenically unsaturated monomers with a primary, secondary or tertiary amino group, in particular monomers of general formula I*

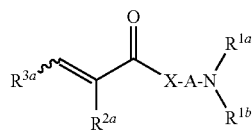

in which
X stands for oxygen or a group N—$R^{4a}$;
A stands for $C_2$-$C_8$-alkylene, e.g. 1,2-ethanediyl, 1,2- or 1,3-propanediyl, 1,4-butanediyl or 2-methyl-1,2-propanediyl, optionally interrupted by 1, 2 or 3 nonadjacent oxygen atoms, as in 3-oxapentane-1,5-diyl;
$R^{1a}$, $R^{1b}$, independently of one another stand for hydrogen, $C_1$-$C_{10}$-alkyl, $C_5$-$C_{10}$-cycloalkyl, phenyl or phenyl-$C_1$-$C_4$-alkyl and in particular both each mean $C_1$-$C_4$-alkyl;
$R^{2a}$ denotes hydrogen or $C_1$-$C_4$-alkyl, in particular hydrogen or methyl;
$R^{3a}$ denotes hydrogen or $C_1$-$C_4$-alkyl and in particular hydrogen; and
$R^{4a}$ denotes hydrogen or $C_1$-$C_4$-alkyl and in particular hydrogen.

Examples of monomers of formula I* are 2-(N,N-dimethylamino)ethyl acrylate, 2-(N,N-dimethylamino)ethylmethacrylate, 2-(N,N-dimethylamino)ethylacrylamide, 3-(N,N-dimethylamino)propyl acrylate, 3-(N,N-dimethylamino)propylmethacrylate, 3-(N,N-dimethylamino)propylacrylamide, 3-(N,N-dimethylamino)propylmethacrylamide and 2-(N,N-dimethylamino)ethylmethacrylamide, with 3-(N,N-dimethylamino)propylmethacrylate being especially preferred.

Preferred basic monomers M1*a are the monomers of general formula I*.

The monomers M1*a include, in addition, anionic or acidic monoethylenically unsaturated monomers. Examples are:
monoethylenically unsaturated monomers, having a sulfonic acid group, and the salts of said monomers, in particular the alkali metal salts, e.g. the sodium or potassium salts and the ammonium salts. This includes ethylenically unsaturated sulfonic acids, in particular vinylsulfonic acid, 2-acrylamido-2-methylpropanesulfonic acid, 2-acryloxyethanesulfonic acid and 2-methacryloxyethanesulfonic acid, 3-acryloxy- and 3-methacryloxypropanesulfonic acid, vinylbenzenesulfonic acid and salts thereof;
ethylenically unsaturated phosphonic acids, such as vinylphosphonic acid and vinylphosphonic acid dimethyl esters and salts thereof; and
monoethylenically unsaturated monomers, bearing one or two carboxyl groups, e.g. α,β-ethylenically unsaturated $C_3$-$C_8$-mono- and $C_4$-$C_8$-dicarboxylic acids, in particular acrylic acid, methacrylic acid, crotonic acid, maleic acid, fumaric acid and itaconic acid.

Preferred acidic monomers M1*a are the aforementioned monoethylenically unsaturated monomers with one or two carboxyl groups.

As well as the monomers M1*a, the polymerizate can also contain up to <80 wt. % of ethylenically unsaturated monomers incorporated by polymerization, which are different from the monomers M1*a. Preferably these are neutral, monoethylenically unsaturated monomers M1*b, which have limited solubility in water preferably of not more than 30 g/l and in particular not more than 20 g/l at 25° C. and 1 bar. It is presumed that as a result of hydrophobic interactions, these monomers promote the formation of the active substance-polymer aggregates. Therefore based on the total weight of the monomers M1*, the polymers P1* preferably contain up to 10 to 75 wt. %, in particular up to 20 to 70 wt. %, especially preferably 30 to 70 wt. % and especially 40 to 65 wt. % of the monomers M1*b, incorporated by polymerization.

The monomers M1*b include in particular monomers of general formula II*

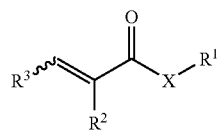

in which
X stands for oxygen or a group N—$R^4$;
$R^1$ stands for $C_1$-$C_{10}C_{20}$-alkyl, $C_5$-$C_{10}$-cycloalkyl, phenyl, or phenyl-$C_1$-$C_4$-alkyl or phenoxy-$C_1$-$C_4$-alkyl;
$R^2$ denotes hydrogen or $C_1$-$C_4$-alkyl;
$R^3$ denotes hydrogen or $C_1$-$C_4$-alkyl; and
$R^4$ denotes hydrogen or $C_1$-$C_4$-alkyl.

Preferred monomers of general formula II* are those in which $R^3$ in formula II* stands for hydrogen. In formula II*, $R^2$ preferably stands for hydrogen or methyl. X in formula II* preferably stands for O, NH, $NCH_3$ or $NC_2H_5$, and especially preferably for O.

$R^1$ in formula II* preferably stands for
$C_2C_1$-$C_{10}C_{20}$-alkyl, in particular $C_1$-$C_{10}$-alkyl such as ethyl, n-propyl, iso-propyl, n-butyl, 2-butyl, isobutyl, tert.-butyl, 1-pentyl, 2-pentyl, neopentyl, n-hexyl, 2-hexyl, n-octyl, 2-ethylhexyl, 2-propylheptyl or, n-decyl, lauryl or stearyl,
$C_5$-$C_{10}$-cycloalkyl such as cyclopentyl, cyclohexyl or methylcyclohexyl, or phenyl-$C_1$-$C_4$-alkyl such as benzyl, 1- or 2-phenylethyl, 1-, 2- or 3-phenylpropyl or phenoxy-$C_2$-$C_4$-alkyl such as 2-phenoxyethyl.

In particular, $R^1$ stands for $C_2$-$C_{10}$-alkyl. Also preferably, $R^1$ stands for methyl or 2-phenoxyethyl.

Especially preferred monomers of formula II* are the esters of acrylic acid with $C_2$-$C_{10}$-alkanols (=$C_2$-$C_{10}$-alkyl acrylates) such as ethyl acrylate, n-butyl acrylate, isobutyl acrylate, tert.-butyl acrylate, n-hexyl acrylate, 2-ethylhexyl acrylate and 3-propylheptyl acrylate, the esters of methacrylic acid with $C_1$-$C_{10}$-alkanols such as methylmethacrylate, ethylmethacrylate, n-butylmethacrylate, isobutylmethacrylate, tert.-butylmethacrylate and n-hexylmethacrylate. Preferred monomers M1*a M1*b are moreover esters of acrylic acid and methacrylic acid with 2-phenoxyethanol such as 2-phenoxyethyl acrylate. Preferred monomers M1*b are moreover the N—($C_2$-$C_{10}$-alkyl)amides of acrylic acid and methacrylic acid and the N—(C$_1$-C$_2$-alkyl)-N—(C$_2$-C$_{10}$-alkyl)amides of acrylic acid and methacrylic acid, e.g. N-ethylacrylamide, N,N-diethylacrylamide, N-butylacrylamide, N-methyl-N-propylacrylamide, N-(n-hexyl)acrylamide, N-(n-octylacrylamide) and the corresponding methacrylamides. In particular the monomers M1*b comprise at least 50 wt. %, in particular at least 70 wt. %, based on the total amount of monomers M1*a, of at least one C$_1$-C$_4$-alkylmethacrylate (R$^1$═C$_1$-C$_4$-alkyl, R$^2$═CH$_3$ and R$^3$═H), and especially preferred among these, methylmethacrylate and tert.-butylmethacrylate.

The monomers M1*b include furthermore vinylaromatic monomers such as styrene, α-methylstyrene, vinyltoluene, etc., olefins with 2 to 20 carbon atoms, preferably α-olefins with 3 to 10 carbon atoms such as propene, 1-butene, 1-pentene, 1-hexene, 1-octene, diisobutene and 1-decene, vinyl esters of aliphatic carboxylic acids such as vinylacetate, vinylpropionate, vinyllaurate, vinylnonanoate, vinyldecanoate, vinyllaurate and vinylstearate, halogenated olefins such as vinylchloride, C$_{11}$-C$_{20}$-alkyl esters of monoethylenically unsaturated monocarboxylic acids with preferably 3 to 6 carbon atoms, e.g. C$_{11}$-C$_{20}$-alkyl acrylates and C$_{11}$-C$_{20}$-alkylmethacrylates such as lauryl acrylate, laurylmethacrylate, isotridecyl acrylate, isotridecylmethacrylate, stearyl acrylate, stearylmethacrylate, di-C$_1$-C$_{20}$-alkyl esters of ethylenically unsaturated dicarboxylic acids with preferably 4 to 8 carbon atoms, e.g. di-C$_1$-C$_{20}$-alkyl esters of fumaric acid and of maleic acid such as dimethylfumarate, dimethylmaleate, dibutylfumarate and dibutylmaleate, glycidyl esters of monoethylenically unsaturated monocarboxylic acids with preferably 3 to 6 carbon atoms, such as glycidyl acrylate and glycidylmethacrylate.

Preferred monomers M1*b are the monomers of general formula II* and furthermore vinyl-aromatic monomers and among these in particular styrene. Preferred monomers M1*b are also mixtures of the aforementioned monomers M1*b, which primarily comprise in particular at least 60 wt. % and especially preferably 70 wt. %, e.g. 60 to 99 wt. % or 70 to 99 wt. %, based on the total amount of the monomers M1*b, of monomers of general formula II* or a mixture of monomers II with styrene and at least one monomer M1*b different from that.

In addition to the monomers M1*a and M1*b, the polymers P1* can contain up to 20 wt. %, in particular not more than 10 wt. %, based on the total amount of the monomers M1*, of ethylenically unsaturated monomers M1*c, which are different from the monomers M1*a and M1*b, incorporated by polymerization.

The monomers M1*c include, furthermore, monoethylenically unsaturated monomers

M1*c.k, which have at least one cationic group. The monomers M1*c.k include in particular those that have a quaternary ammonium group or a quaternized imino group. Examples of monomers with a quaternized imino group are N-alkylvinylpyridinium salts and N-alkyl-N'-vinylimidazolinium salts such as N-methyl-N'-vinylimidazolinium chloride or metosulfate. Among the monomers M1*c.k, the monomers of general formula III* are especially preferred

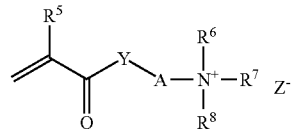

in which

R$^5$ stands for hydrogen or C$_1$-C$_4$-alkyl, in particular hydrogen or methyl, R$^6$, R$^7$ and R$^8$, independently of one another, stand for C$_1$-C$_4$-alkyl, in particular methyl, and Y stands for oxygen, NH or NR$^9$ with R$^9$═C$_1$-C$_4$-alkyl, A stands for C$_2$-C$_8$-alkylene, e.g. 1,2-ethanediyl, 1,2- or 1,3-propanediyl, 1,4-butanediyl or 2-methyl-1,2-propanediyl, which is optionally interrupted by 1, 2 or 3 nonadjacent oxygen atoms, such as in 3-oxapentane-1,5-diyl, and Z$^−$ stands for an anion equivalent, e.g. for Cl$^−$, HSO$_4$, ½SO$_4^{2−}$ or CH$_3$OSO$_3^−$ etc.

Examples of said monomers M1*c.k are 2-(N,N,N-trimethylammonium)ethyl acrylate-chloride, 2-(N,N,N-trimethylammonium)ethylmethacrylate-chloride, 2-(N,N,N-trimethylammonium)ethylmethacrylamide-chloride, 3-(N,N,N-trimethylammonium)propyl acrylate-chloride, 3-(N,N,N-trimethylammonium)propylmethacrylate-chloride, 3-(N,N,N-trimethylammonium)propylacrylamide-chloride, 3-(N,N,N-trimethylammonium)propylmethacrylamide-chloride, 2-(N,N,N-trimethylammonium)ethylacrylamide-chloride, and the corresponding metosulfates and sulfates.

The proportion of monomers M1*c.k in the monomers M1* is advantageously not more than 20 wt. %, e.g. 0.1 to 20 wt. %, in particular 0.5 to 15 wt. %, and especially 1 to 10 wt. %. In a preferred embodiment the polymer P1* contains no or not more than 0.1 wt. % of monomers M1*c.k incorporated by polymerization.

The monomers M1*c also include monomers M1*c.v, which have two or more, unconjugated ethylenically unsaturated double bonds. The proportion of such monomers M1*c.v is as a rule not more than 2 wt. % and in particular not more than 0.5 wt. %, based on the total amount of monomer M1*.

Examples are vinyl and allyl esters of monoethylenically unsaturated carboxylic acids such as allyl acrylate and allylmethacrylate, di- and polyacrylates of di- or polyols such as ethylene glycol diacrylate, ethylene glycol dimethacrylate, butanedioldiacrylate, butanedioldimethacrylate, hexanedioldiacrylate, hexanedioldimethacrylate, triethylene glycol diacrylate, triethylene glycol trimethacrylate, tris (hydroxymethyl)ethane-triacrylate and -trimethacrylate, pentaerythritol-triacrylate and -trimethacrylate, furthermore the allyl- and methallylesters of polyfunctional carboxylic acids, such as diallylmaleate, diallylfumarate, diallylphthalate. Typical monomers M1*c.3 are also compounds, such as divinylbenzene, divinylurea, diallylurea, triallylcyanurate, N,N'-divinyl- and N,N'-diallylimidazolidin-2-one, and methylene bisacrylamide and methylene bismethacrylamide.

In an especially preferred embodiment 2a the polymer P1* contains, based on the total amount of the monomers M1*, 20 to 80 wt. %, in particular 25 to 60 wt. % of basic monomers M1*a, and
20 to 80 wt. %, in particular 40 to 75 wt. % of monomers M1*b incorporated by polymerization.

In embodiment 2a, the preferred monomers M1*a are vinyl-substituted nitrogen heteroaromatics, especially the aforementioned vinylpyridines and the monomers of formula I*. Especially preferred monomers M1*a are the monomers of formula I*.

In embodiment 2a, the preferred monomers M1*b are the monomers of general formula II and furthermore vinylaromatic monomers and of these in particular styrene. Preferred monomers M1*b are also mixtures of the aforementioned monomers M1*b, which comprise primarily, in particular at least 60 wt. % and especially preferably 70 wt. %, e.g. 60 to 99 wt. % or 70 to 99 wt. %, based on the total amount of the monomers M1*b, of monomers of general formula II or a mixture of monomers II with styrene and at least one monomer M1*b different from that. In particular the monomers M1*b comprise exclusively or almost exclusively (>95 wt. %) monomers of general formula II and especially a mixture of two or more different esters of acrylic acid or methacrylic acid ($R^2$=H or methyl, $R^3$=H and X=O).

In a preferred embodiment the monomers M1*b comprise a mixture of a $C_1$-$C_4$-alkylmethacrylate such as methylmethacrylate with a phenyl-$C_1$-$C_4$-alkyl(meth)acrylate or phenoxy-$C_1$-$C_4$-alkyl(meth)acrylate, e.g. with 2-phenoxyethylmethacrylate.

In another especially preferred embodiment 3a the polymer P1 contains, based on the total amount of the monomers M1*,
20 to 80 wt. %, in particular 25 to 60 wt. % of monomers M1*a bearing carboxyl groups,
and 20 to 80 wt. %, in particular 40 to 75 wt. % of monomers M1*b incorporated by polymerization.

In embodiment 3a, the preferred monomers M1*a are monoethylenically unsaturated mono- and dicarboxylic acids, especially acrylic acid, methacrylic acid, itaconic acid, maleic acid and fumaric acid.

In embodiment 3a the preferred monomers M1*b are monomers of general formula II, $C_2$-$C_{10}$-olefins and vinyl aromatics in particular styrene, $C_1$-$C_8$-alkylmethacrylates such as methylmethacrylate, n-butylmethacrylate, tert-butylmethacrylate, n-hexylmethacrylate and 2-ethylhexylmethacrylate.

The polymers P1*bear reactive functional groups R1, which react with the isocyanate groups, forming bonds. The average number of such groups per polymer molecule (functionality) is as a rule not more than two 3, often not more than 2 and is for example in the range from 0.3 to 3, often in the range from 0.5 to 2, or preferably in the range from 0.3 to 1.8, in particular in the range from 0.5 to 1.5 and especially in the range from 0.6 to 1.4. The functional group R1 can be arranged in the polymer chain and is preferably located at the end of the polymer chain.

The hydrophobic polymer P1* preferably has a number-average molecular weight determined by GPC by the usual methods in the range from 500 to 20000 dalton and in particular in the range from 1500 to 15000 dalton.

The polymers P2* are linear or branched poly-$C_2$-$C_4$-alkylene ethers, thus polymers that are made up essentially, i.e. to at least 90 wt. %, based on the weight of the polymers P2*, from repeating units of formula IV

 (IV)

in which A stands for a $C_2$-$C_4$-alkylene group such as ethane-1,2-diyl, propane-1,2-diyl, propane-1,3-diyl, butane-1,2-diyl or butane-1,3-diyl. Among the polymers P2*, those are preferred that are made up to at least 50 wt. %, advantageously at least 70 wt. %, in particular at least 80 wt. % and especially to at least 90 wt. % from ethylene oxide units, i.e. from groups with the formula IV, in which A stands for 1,2-ethanediyl. Moreover, the aliphatic polyethers can have structural units that are derived from $C_3$-$C_4$-alkylene oxides.

Preferred among the polymers P2* are in particular those having, with respect to the functional groups R2, a functionality F2 in the range from 0.5 to 3 and in particular in the range from 0.6 to 2.5.

The number-average molecular weight of the polymers P2*, determined by GPC by the usual methods, is preferably in the range from 500 to 20000 dalton and in particular in the range from 800 to 15000 dalton.

Especially preferred polyethers P2* are those of general formula V

 (V)

in which
$R^a$ stands for hydrogen, $C_1$-$C_{20}$-alkyl or benzyl,
X denotes oxygen or NH,
$R^b$ denotes hydrogen or methyl, with at least 50 mol. %, in particular at least 70 mol. % and preferably at least 90 mol. % of the groups Rb standing for hydrogen,
p denotes an integer, the average value of which is in the range from 10 to 500, preferably 20 to 250 and in particular 25 to 100 (number-average).

Suitable polyethers P2* are known by a person skilled in the art and for the most part are commercially available, for example under the trade names Pluriol® and Pluronic® (polyethers from BASF-Aktiengesellschaft).

The total fraction of polymers P1* in the aforementioned polymer composition, i.e. the total amount of reacted and unreacted polymer P1*, is preferably 9 to 90 and in particular 20 to 68 wt. % of the total weight of polymer P1*, polyether P2* and compound V.

The total fraction of polyethers P2* in the polymer composition, i.e. the total amount of reacted and unreacted polyether P2*, is preferably 9 to 90 and in particular 30 to 78 wt. % of the total weight of polymer P1*, polyether P2* and compound V.

The total fraction of compound V in the polymer composition, i.e. the total amount of compound V used, is preferably 1 to 20 and in particular 2 to 15 wt. % of the total weight of polymer P1*, polyether P2* and compound V.

The weight ratio of polymer P1* to polyether P2* in the amphiphilic polymer composition, calculated in each case as the total amount of polymers used for production, is preferably in the range from 1:10 to 10:1 and in particular in the range from 1:4 to 2.2:1.

Compounds V have already been defined above. the preferences mentioned above also apply here.

The aforementioned polymer compositions and methods for the production of the aforementioned polymer compositions are described in WO06/084680.

The aforementioned polymer compositions are designated hereinafter as "Polymers A".

Furthermore, random radical copolymers are suitable as matrix-forming inactive ingredients, as described in WO05/046328, containing as monomers at least one olefinically unsaturated sulfonic acid of formula I**

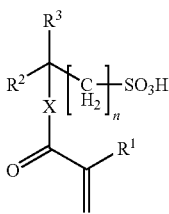

where X denotes oxygen or NR$^5$, R$^1$ denotes hydrogen or methyl, n can have a value from 0 to 10 and R$^2$ and R$^3$, independently of one another, denote C$_1$- to C$_6$-alkyl, R$^5$ denotes hydrogen, alkyl, aryl, alkaryl, aralkyl, alkoxyalkyl, aryloxyalkyl, alkoxyaryl, hydroxyalkyl, (di)alkylaminoalkyl, (di)alkylaminoaryl, (di)arylaminoalkyl, alkarylaminoalkyl, alkarylaminoaryl, where the aryl residues can be substituted, and the olefinic unsaturated sulfonic acid can be in the form of acid or salt or as a mixture of the acid and salt form, at least one olefinically unsaturated monomer of formula II**

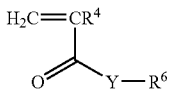

where Y denotes oxygen or NR$^5$, R$^4$ denotes hydrogen or methyl, R$^5$ and R$^6$, independently of one another, denote hydrogen, alkyl, aryl, alkaryl, aralkyl, alkoxyalkyl, aryloxyalkyl, alkoxyaryl, hydroxyalkyl, (di)alkylaminoalkyl, (di)alkylaminoaryl, (di)arylaminoalkyl, alkarylaminoalkyl, alkarylaminoaryl, and
optionally other monomers.

Salts of the sulfonic acid of formula I** are preferably alkali-metal or ammonium salts. As alkyl residues, alone or in the stated combinations, consideration may be given to C$_1$ to C$_{20}$-alkyl. We should mention in particular C$_1$- to C$_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 1,1,2-trimethylpropyl, 1,2,2-trimethylpropyl, 1-ethyl-1-methylpropyl and 1-ethyl-2-methylpropyl, cyclohexyl, n-heptyl, n-octyl, 2-ethylhexyl, decyl, isodecyl, undecyl, lauryl, tridecyl, myristyl, pentadecyl, cetyl, heptadecyl, stearyl.

"Aryl residues" means mononuclear or polynuclear, optionally substituted aromatic hydrocarbon residues. For example we may mention phenyl, naphthyl, or phenyl substituted with halogen such as fluorine or chlorine.

Alkoxy stands for an alkyl residue, which is bound to the backbone via an oxygen atom (—O—).

Aryloxy stands for an aryl residue, which is bound to the backbone via an oxygen atom (—O—).

The following, for example, can be present as further monomers: vinylaromatic monomers such as styrene and styrene derivatives such as α-methylstyrene, vinyltoluene, ortho-, meta- and para-methylstyrene, ethylvinylbenzene, vinylnaphthalene, vinylxylene and the corresponding halogenated vinylaromatic monomers, vinylaromatic monomers bearing nitro, alkoxy, haloalkyl, carbalkoxy, carboxy, amino and alkylamino groups, α-olefins such as ethene, propene, 1-butene, 1-pentene, 1-hexene, isobutene, long-chain (C$_{10}$-C$_{20}$) alkyl-α-olefins, dienes such as butadiene and isoprene, vinylalcohol esters such as vinylacetate, vinyl halides such as vinylchloride, vinylbromide, vinylfluoride, vinylidene chloride, vinylidene fluoride, vinylidene bromide, vinylnitrile, vinylcarboxylates, 1-vinylamides such as 1-vinylpyrrolidone, 1-vinylpiperidone, 1-vinylcaprolactam, 1-vinylformamide, 1-vinylacetamide or 1-methyl-1-vinylacetamide, N-vinylimidazole, C$_1$-C$_{24}$-alkyl esters and singly and doubly substituted and unsubstituted C$_1$-C$_{24}$-alkylamides of monoethylenically unsaturated monomers such as acrylic, methacrylic, fumaric, maleic, and itaconic acids, vinylsulfonic acid, anhydrides such as maleic acid anhydride, unsaturated aldehydes such as acrolein, unsaturated ethers such as 1,4-cyclohexane-dimethanoldivinyl ether, 1,4-cyclohexane-dimethanolmonovinyl ether, butanedioldivinyl ether, butanediolmonovinyl ether, cyclohexylvinyl ether, diethylene glycol divinyl ether, ethylene glycol monovinyl ether, ethylvinyl ether, methylvinyl ether, n-butyl-vinyl ether, octadecylvinyl ether, triethylene glycol vinylmethyl ether, vinylisobutyl ether, vinyl-(2-ethylhexyl) ether, vinylpropyl ether, vinylisopropyl ether, vinyldodecyl ether, vinyltert-butyl ether, hexadioldivinyl ether, hexadiolmonovinyl ether, diethylene glycol monovinyl ether, diethylaminoethylvinyl ether, polytetrahydrofuran-290-divinyl ether, tetraethylene glycol divinyl ether, ethylene glycol butylvinyl ether, ethylene glycol divinyl ether, triethylene glycol divinyl ether, trimethylolpropane trivinyl ether, aminopropylvinyl ether.

A polymer designated as "radical" means a polymer produced by radical polymerization.

A copolymer designated as "random" means a copolymer in which the monomer sequence is determined by the copolymerization parameters of the monomers. This also applies appropriately to copolymers consisting of more than two types of monomers.

Polymers of this type are also called random copolymers.

The sulfonic acids of formula I** can be in the form of acids or salts or as a mixture of the acid and salt forms. The term "sulfonic acid" will be used to represent all these forms.

Salts of sulfonic acid are metal salts, in particular alkali metal salts such as lithium, sodium or potassium salts or ammonium salts.

In a preferred embodiment the random radical copolymer contains, as monomers, at least one olefinically unsaturated sulfonic acid of formula I, at least one (meth)acrylate of formula IIa

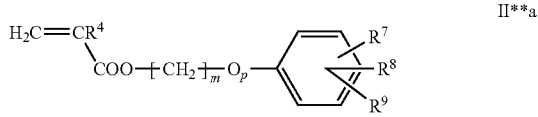

where m denotes integers from 0 to 4 and p denotes the integers 0 or 1, R$^4$ denotes hydrogen or methyl and R$^7$, R$^8$ and R$^9$, independently of one another, denote hydrogen, C$_1$ to C$_6$-alkyl, halogen, hydroxy, C$_1$ to C$_6$-alkoxy, where alkyl and alkoxy can be halogen-substituted, and optionally other olefinic monomers of formula II**b

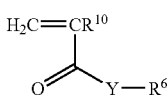

where Y=O or $NR^5$, $R^{10}$ is hydrogen or methyl, $R^5$, $R^6$ denote hydrogen, alkyl, aryl, alkaryl, aralkyl, alkoxyalkyl, aryloxyalkyl, alkoxyaryl, hydroxyalkyl, (di)alkylaminoalkyl, (di)alkylaminoaryl, (di)arylaminoalkyl, alkarylaminoalkyl, alkarylaminoaryl, where the aryl residues can be substituted. Alkoxy stands for an alkyl residue as stated above, which is bound to the backbone via an oxygen atom. Aryloxy stands for an aryl residue, which is bound to the backbone via an oxygen atom (—O—).

"Aryl residues" means mononuclear or polynuclear, optionally substituted aromatic hydrocarbon residues. For example, we may mention phenyl, naphthyl, or phenyl substituted with halogen such as fluorine or chlorine.

Aryloxy stands for an aryl residue as stated above, which is bound to the backbone via an oxygen atom.

For example, alkaryl stands for tolyl, aralkyl for benzyl, alkoxyalkyl for ethoxyethyl, aryloxyalkyl for phenoxyethyl, alkoxyaryl for methoxyphenyl, hydroxyalkyl for hydroxyethyl, (di)alkylaminoalkyl for dimethylaminopropyl.

In an especially preferred embodiment the random radical copolymer is made up of at least one olefinically unsaturated sulfonic acid of formula I** and phenoxy-$C_1$-$C_6$-alkyl acrylate, for example phenoxyethyl acrylate.

In another preferred embodiment the random radical copolymer is made up of monomers with the aforementioned formula I, in particular 2-acrylamido-2-methyl-1-propanesulfonic acid and at least one olefinically unsaturated monomer of formula IIc

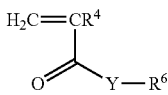

where Y stands for oxygen or $NR^5$, $R^4$ stands for hydrogen or methyl, $R^5$, $R^6$ stand for hydrogen, alkyl, aryl, alkaryl, aralkyl, alkoxyalkyl, aryloxyalkyl, alkoxyaryl, hydroxyalkyl, (di)alkylaminoalkyl, (di)alkylaminoaryl, (di)arylaminoalkyl, alkarylaminoalkyl, alkarylaminoaryl, where alkyl and aryl have the meanings stated previously, and optionally other monomers.

In another especially preferred embodiment the random radical copolymer contains, as monomers, 2-acrylamido-2-methyl-1-propanesulfonic acid and at least one olefinically unsaturated monomer of formula II, where Y denotes oxygen, $R^4$ denotes hydrogen and $R^6$ denotes hydrogen or alkyl.

Accordingly, the random radical copolymer in this especially preferred embodiment contains, as monomers, 2-acrylamido-2-methyl-1-propanesulfonic acid and at least one ester of acrylic acid.

Said esters of acrylic acid are for example methyl acrylate, ethyl acrylate, propyl acrylate, isopropyl acrylate, butyl acrylate, 2-methylpropyl acrylate, tert-butyl acrylate, hexyl acrylate, cyclohexyl acrylate, n-octyl acrylate, 2-ethylhexyl acrylate, decyl acrylate, isodecyl acrylate, undecyl acrylate, lauryl acrylate, tridecyl acrylate, myristyl acrylate, pentadecyl acrylate, cetyl acrylate, heptadecyl acrylate, stearyl acrylate.

In a quite especially preferred embodiment the random radical copolymer contains, as monomers, 2-acrylamido-2-methyl-1-propanesulfonic acid, phenoxyethyl acrylate and at least one ester of acrylic acid.

In another quite especially preferred embodiment the random radical copolymer is made up of the monomers 2-acrylamido-2-methyl-1-propanesulfonic acid and phenoxyethyl acrylate.

Methods for the production of the aforementioned copolymers are described in WO05/046328.

The aforementioned copolymers are designated hereinafter as "Polymers B".

Furthermore, suitable matrix-forming inactive ingredients are copolymers as described in WO 06/000592, which can be obtained by copolymerization of (A) optionally at least one ethylenically unsaturated mono- or dicarboxylic acid or at least one anhydride derived from a mono- or dicarboxylic acid, (B) at least one hydrophobic monomer that has aromatic functions or aliphatic functions or aromatic and aliphatic functions, (C) at least one allyl alcohol alkoxylate, (D) optionally other monoethylenically unsaturated monomers.

Examples of ethylenically unsaturated mono- or dicarboxylic acids with 3 to 8 carbon atoms are (meth)acrylic acid, maleic acid, fumaric acid, crotonic acid; acrylic acid is quite especially preferred.

As anhydrides derived from a mono- or dicarboxylic acid with 3 to 8 carbon atoms, we may mention for example: maleic acid anhydride, itaconic acid anhydride, citraconic acid anhydride, methylene-malonic acid anhydride, preferably itaconic acid anhydride and maleic acid anhydride and quite especially preferably maleic acid anhydride.

Mixed anhydrides may also be considered, for example the mixed anhydride of (meth)acrylic acid and acetic acid.

Preferred polymerizates can be obtained by copolymerization of the following monomers:

(A) optionally at least one ethylenically unsaturated mono- or dicarboxylic acid with 3 to 8 carbon atoms and/or at least one anhydride derived from a mono- or dicarboxylic acid with 3 to 8 carbon atoms, (B) at least one vinyl-aromatic compound, for example of general formula VIII

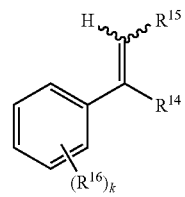

in which $R^{14}$ and $R^{15}$, independently of one another, each stand for hydrogen, methyl or ethyl, $R^{16}$ denotes methyl or ethyl and k denotes an integer from 0 to 2; preferably $R^{14}$ and $R^{15}$ are each hydrogen, and preferably k=0.

Alpha-methylstyrene is preferably used as (B), and quite especially preferably styrene.

(C) at least one alkoxylated unsaturated ether of general formula I*

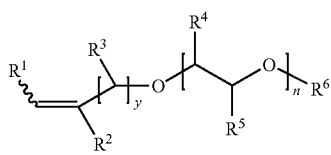

I the variables in formula I* being defined as follows:
$R^1, R^2, R^3$ may be identical or different and are selected from hydrogen, $C_1$-$C_4$-alkyl such as methyl, ethyl, n-propyl, iso-propyl, n-butyl, iso-butyl, sec.-butyl and tert.-butyl, especially preferably methyl, or hydrogen;
$R^4, R^5$ each identical or different, and selected from hydrogen, $C_1$-$C_4$-alkyl such as methyl, ethyl, n-propyl, iso-propyl, n-butyl, iso-butyl, sec.-butyl and tert.-butyl, especially preferably methyl, or hydrogen;
$R^6$ selected from hydrogen, $SO_3M$, $PO_3M_2$ and preferably organic residues such as $C_1$-$C_{30}$-alkyl, preferably linear or branched, such as methyl, ethyl, n-propyl, iso-propyl, n-butyl, iso-butyl, sec.-butyl, tert.-butyl, n-pentyl, iso-pentyl, sec.-pentyl, neo-pentyl, 1,2-dimethylpropyl, iso-amyl, n-hexyl, iso-hexyl, sec.-hexyl, n-heptyl, n-octyl, n-nonyl, n-decyl, n-dodecyl, n-hexadecyl, n-octadecyl, n-eicosyl; especially preferably $C_1$-$C_4$-alkyl such as methyl, ethyl, n-propyl, iso-propyl, n-butyl, iso-butyl, sec.-butyl and tert.-butyl; CO—H (formyl) or CO—$C_1$-$C_{20}$-alkyl, especially preferably acetyl, propionyl, n-butyryl, n-stearyl, n-lauryl; CO—$C_6$-$C_{14}$-aryl, for example alpha-naphthoyl, beta-naphthoyl and preferably benzoyl CO—$C_6H_5$,
M alkali metal, especially sodium or potassium, or NH4+, or $CH_3$,
n is an integer from 3 to 100, preferably from 10 to 40,
y is an integer from 0 to 10, preferably 1 to 10 and especially preferably 1 or 2.

Especially preferably, $R^4$ and $R^5$ are each hydrogen.

Especially preferably, $R^1$ and $R^3$ are hydrogen, $R^2$ is selected from hydrogen or methyl, and y is 1.

Optionally, one or more additional monoethylenically unsaturated monomers (D) can be incorporated by polymerization.

The monomer or monomers (D), which can optionally be in the polymerizates incorporated by polymerization, are different from (A). As preferred monomers (D) we may mention:
ethylenically unsaturated $C_3$-$C_8$-carboxylic acid derivatives of general formula II

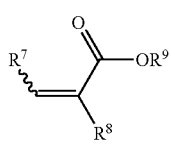

II acrylamides of formula III*,

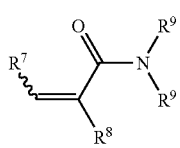

III noncyclic amides of general formula IVa and cyclic amides of general formula IVb

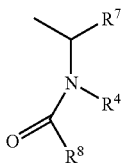

IVa

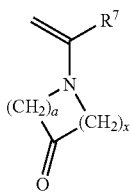

IVb $C_1$-$C_{20}$-alkylvinyl ethers such as methylvinyl ether, ethylvinyl ether, n-propylvinyl ether, isopropylvinyl ether, n-butylvinyl ether, isobutylvinyl ether, 2-ethylhexylvinyl ether or n-octadecylvinyl ether;

N-vinyl derivatives of nitrogen-containing aromatic compounds, preferably N-vinylimidazole, 2-methyl-1-vinylimidazole, N-vinyloxazolidone, N-vinyltriazole, 2-vinylpyridine, 4-vinylpyridine, 4-vinylpyridine-N-oxide, N-vinylimidazoline, N-vinyl-2-methylimidazoline, alkoxylated unsaturated ethers of general formula V,

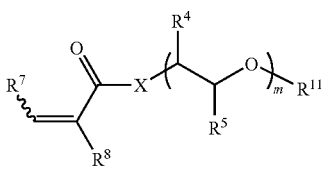

V esters and amides of general formula VI

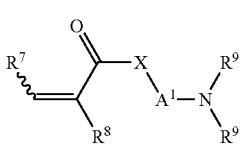

VI unsaturated esters of general formula VII

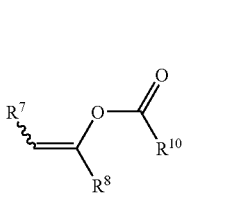

VII

Further suitable are monomers containing sulfonate, phosphate or phosphonate groups, for example vinylsulfonic acid and vinylphosphonic acid and compounds of general formula IX

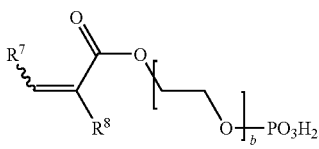

where phosphate groups, sulfonate groups or phosphonate groups can optionally be present partially or entirely in the form of alkali metal salts, the variables being defined as follows:

$R^7$ selected from linear or branched $C_1$-$C_{10}$-alkyl, such as methyl, ethyl, n-propyl, iso-propyl, n-butyl, iso-butyl, sec.-butyl, tert.-butyl, n-pentyl, iso-pentyl, sec.-pentyl, neo-pentyl, 1,2-dimethylpropyl, iso-amyl, n-hexyl, iso-hexyl, sec.-hexyl, n-heptyl, n-octyl, n-nonyl, n-decyl; especially preferably $C_1$-$C_4$-alkyl such as methyl, ethyl, n-propyl, iso-propyl, n-butyl, iso-butyl, sec.-butyl and tert.-butyl, and especially hydrogen;

$R^8$ selected from linear or branched $C_1$-$C_{10}$-alkyl, such as methyl, ethyl, n-propyl, iso-propyl, n-butyl, iso-butyl, sec.-butyl, tert.-butyl, n-pentyl, iso-pentyl, sec.-pentyl, neo-pentyl, 1,2-dimethylpropyl, iso-amyl, n-hexyl, iso-hexyl, sec.-hexyl, n-heptyl, n-octyl, n-nonyl, n-decyl; especially preferably $C_1$-$C_4$-alkyl such as methyl, ethyl, n-propyl, iso-propyl, n-butyl, iso-butyl, sec.-butyl and tert.-butyl, especially methyl and especially hydrogen;

$R^9$ identical or different and $C_1$-$C_{22}$-alkyl, linear or branched, such as methyl, ethyl, n-propyl, iso-propyl, n-butyl, iso-butyl, sec.-butyl, tert.-butyl, n-pentyl, iso-pentyl, sec.-pentyl, neo-pentyl, 1,2-dimethylpropyl, iso-amyl, n-hexyl, iso-hexyl, sec.-hexyl, n-heptyl, n-octyl, n-nonyl, n-decyl, n-dodecyl, n-eicosyl; especially preferably $C_1$-$C_4$-alkyl such as methyl, ethyl, n-propyl, iso-propyl, n-butyl, iso-butyl, sec.-butyl and tert.-butyl or hydrogen; with the proviso that, in formula II, R9 does not stand for hydrogen;

A1 identical or different and $C_2$-$C_6$-alkylene, for example —$CH_2$—, —$CH(CH_3)$—, —$(CH_2)_2$—, —$CH_2$—$CH(CH_3)$—, —$(CH_2)_3$—, —$CH_2$—$CH(C_2H_5)$—, —$(CH_2)_4$—, —$(CH_2)_5$—, —$(CH_2)_6$—, preferably $C_1$-$C_3$-alkylene; especially —$(CH_2)_2$—, $CH_2$—$CH(CH_3)$— and —$CH_2$—$CH(C_2H_5)$—;

x an integer in the range from 2 to 6, preferably 3 to 5;

a an integer in the range from 0 to 6, preferably in the range from 0 to 2;

b an integer in the range from 1 to 40, preferably 1 to 10, m an integer in the range from 2 to 200, preferably 10 to 40;

$R^{10}$, $R^{11}$ may be identical or different and are selected from hydrogen, linear or branched $C_1$-$C_{10}$-alkyl, with linear and branched $C_1$-$C_{10}$-alkyl being defined as above;

X is oxygen or N—$R^{12}$;

$R^{12}$ is selected from linear or branched $C_1$-$C_{10}$-alkyl, such as methyl, ethyl, n-propyl, iso-propyl, n-butyl, iso-butyl, sec.-butyl, tert.-butyl, n-pentyl, iso-pentyl, sec.-pentyl, neo-pentyl, 1,2-dimethylpropyl, iso-amyl, n-hexyl, iso-hexyl, sec.-hexyl, n-heptyl, n-octyl, n-nonyl, n-decyl,-hexyl; and especially hydrogen or methyl; phenyl.

The other variables are as defined above.

Selected examples of compounds of formula III* are (meth)acrylamides such as acrylamide, N-methylacrylamide, N,N-dimethylacrylamide, N-ethylacrylamide, N-propylacrylamide, N-tert.-butylacrylamide, N-tert.-octylacrylamide, N-undecylacrylamide or the corresponding methacrylamides.

Selected examples of compounds of formula IVa are N-vinylcarboxylic acid amides such as N-vinylformamide, N-vinyl-N-methylfomamide, N-vinylacetamide or N-vinyl-N-methylacetamide; selected examples of representatives of compounds of formula IV b are N-vinylpyrrolidone, N-vinyl-4-piperidone and N-vinyl-epsilon-caprolactam.

Selected examples of compounds of formula VI are (meth)acrylic acid ester and amides such as N,N-dialkylaminoalkyl(meth)acrylates or N,N-dialkylaminoalkyl(meth)acrylamides; examples are N,N-dimethylaminoethyl acrylate, N,N-dimethylaminoethylmethacrylate, N,N-diethylaminoethyl acrylate, N,N-diethylaminoethylmethacrylate, N,N-dimethylaminopropyl acrylate, N,N-dimethylaminopropylmethacrylate, N,N-diethylaminopropyl acrylate, N,N-diethylaminopropylmethacrylate, 2-(N,N-dimethylamino)ethylacrylamide, 2-(N,N-dimethylamino)ethylmethacrylamide, 2-(N,N-diethylamino)ethylacrylamide, 2-(N,N-diethylamino)ethylmethacrylamide, 3-(N,N-dimethylamino)propylacrylamide and 3-(N,N-dimethylamino)propylmethacrylamide.

Selected examples of compounds of formula VII are vinylacetate, vinylpropionate, vinylbutyrate, vinyl-2-ethyl-hexanoate or vinyllaurate.

Preferably acrylic esters are used as monomers (D).

Quite especially preferably, the following are used as monomer (D): methyl acrylate, methylmethacrylate, acrylamide, vinyl-n-butyl ether, vinyl-iso-butyl ether, N-vinyl-formamide, N-vinylpyrrolidone, 1-vinylimidazole, 4-vinylpyridine, vinylphosphonic acid, vinylsulfonic acid.

Preferably the monomers (A) to (D) are incorporated by polymerization in following amounts:

(A) 0 to 50 wt. % of at least one ethylenically unsaturated mono- or dicarboxylic acid with 3 to 8 carbon atoms or at least one anhydride of a mono- or dicarboxylic acid with 3 to 8 carbon atoms, preferably 5 to 30 wt. %, (B) 5 to 80 wt. % of at least one hydrophobic monomer, preferably 8 to 50 wt. %, (C) 10 to 90 wt. % of at least one alkoxylated unsaturated ether of general formula I, preferably 40 to 75 wt. %, (D) 0 to 20 wt. % of at least one further monomer, preferably 2 to 10 wt. %, quite especially preferably 1 to 5 wt. % the monomers being defined as above.

The aforementioned copolymerizates are designated hereinafter as "Polymers C".

Methods of production of the aforementioned Polymers C are described in WO 06/000592.

It is also possible to use mixtures of the aforementioned matrix-forming inactive ingredients.

Preferred matrix-forming inactive ingredients are Polymers A, and Polymers B and C, vinylpyrrolidone polymers and vinylpyrrolidone-vinylacetate copolymers and mixtures of the aforementioned polymers.

The inactive ingredients of the matrix (ii) are preferably used in amounts from 30 to 90 wt. %.

For further improvement of solubility, solubilizers can additionally be used.

As solubilizers, it is possible to use alkali-metal, alkaline-earth, and ammonium salts of ligninsulfonic acid, naphthalenesulfonic acid, phenolsulfonic acid, dibutylnaphthalenesulfonic acid, alkarylsulfonates, alkyl sulfates, alkyl sulfonates, fatty alcohol sulfates, fatty acids and sulfated fatty alcohol glycol ethers, and consideration may also be given to condensation products of sulfonated naphthalene and naphthalene derivatives with formaldehyde, condensation products of naphthalene or of naphthalenesulfonic acid with phenol and formaldehyde, polyoxyethylene-octylphenol ethers, ethoxylated isooctylphenol, octylphenol, nonylphenol, alkylphenolpolyglycol ethers, tributylphenylpolyglycol ethers, tristearylphenylpolyglycol ethers, alkarylpolyether alcohols, alcohol- and fatty alcohol-ethylene oxide condensates, ethoxylated castor oil, polyoxyethylene alkylethers, ethoxylated polyoxypropylene, lauryl alcohol polyglycolether acetal, sorbitol esters, ligninsulfite spent liquor and methylcellulose, polyoxyethylene fatty acid esters, polyoxyethylene fatty alcohols, polyoxyethylene glycerol fatty acid esters, polyoxyethylene glycerol fatty alcohols, glycerol fatty acid esters, glycerol fatty alcohols, sorbitan fatty acid esters.

Said surfactants (iii) are preferably used in amounts from 0 to 30 wt. %, preferably 1 to 30 wt. %.

It may also be advisable to use organic solvents in amounts of up to 10 wt. % as additional solubilizers. Possible organic solvents are aromatic solvents (e.g. Solvesso products, xylene), paraffins (e.g. petroleum fractions), alcohols (e.g. methanol, butanol, pentanol, benzyl alcohol, iso-propanol), ketones (e.g. cyclohexanone, gamma-butyrolactone), pyrrolidones (NMP, NOP), acetates (glycol diacetate), glycols, dimethyl fatty acid amides, fatty acids and fatty acid esters, DMSO. Basically, solvent mixtures can also be used.

Preferably, however, the use of organic solvents is avoided.

Sometimes the active substances and solubilizers have an appreciable softening effect, i.e. they lower the glass transition temperature of the polymer considerably, so that spray drying occasionally becomes difficult. In these cases it has proved very advantageous to use a carrier (also called adsorbent hereinafter). This carrier absorbs the liquid or semisolid active substance/polymer solution, thus producing a solid preparation which can be used easily. The following substances are examples of carriers that can be used: natural mineral powders (e.g. kaolins, aluminas, talc, chalk, bole, loess, clay, dolomite, diatomaceous earth) and synthetic mineral powders (e.g. silicic acid, finely-divided silicic acid, hydrophobic silicic acid, silicates such as alkali-metal or alkaline-earth silicates, alkaline-earth aluminum silicates, calcium and magnesium sulfate, magnesium oxide), crosslinked polyvinylpyrrolidone, ground plastics, fertilizers, e.g. ammonium sulfate, ammonium phosphate, ammonium nitrate, ureas and vegetable products, such as milled cereals, bark flour, wood flour and nutshell flour, cellulose (cellulose powder), cellulose derivatives such as sodium carboxymethylcellulose, starch, starch derivatives such as crosslinked sodium carboxymethylstarch and other solid carrier substances.

As a rule the adsorbent is suspended in the spray solution before the heating step and dried along with it. However, some can also be injected as powder into the spraying tower.

Furthermore, other inactive ingredients (iv) such as bactericides and/or antifoaming agents and optionally colorants and/or adhesives for seed dressing can be used in order to achieve specific characteristics.

If said inactive ingredients are added, they are preferably contained in amounts from 0 to 50 wt. %, especially preferably in amounts from 0.1 to 20 wt. %.

As antifoaming agents, all the usual antifoaming agents for formulation of agrochemical active substances can be considered. Examples of antifoaming agents are silicone emulsions (e.g. Silikon® SRE, from the company Wacker or Rhodorsil® from the company Rhodia), long-chain alcohols, fatty acids, organofluorine compounds and mixtures thereof.

As bactericides, all the usual bactericides for formulation of agrochemical active substances can be considered, for example bactericides based on diclorophen and benzylalcohol-hemiformal. Examples of bactericides are Proxel® from the company ICI or Acticide® RS from Thor Chemie and Kathon® MK from Rohm & Haas.

As colorants, all the usual colorants for such purposes can be considered. Both pigments with very low solubility in water, and water-soluble dyes can be used. Examples that may be mentioned are the colorants known by the designations Rhodamine B, C.I. Pigment Red 112 and C.I. Solvent Red 1, and pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Adhesives that may be considered are all the binders that can be used in seed dressings. Preferably we may mention polyvinylpyrrolidone, polyvinylacetate, polyvinyl alcohol and tylose.

According to the invention, aqueous solutions containing the pesticide and the inactive ingredients of the matrix and optionally the additional components (iii) to (iv) are first prepared by heating. Preferably water is used as the only solvent. In general, the concentration of the sparingly soluble pesticide in the matrix of inactive ingredients is 1 or more wt. %, preferably more than 10 wt. %, and especially preferably more than 20 wt. %. In one of the preferred embodiments the concentration of the sparingly soluble pesticide in the matrix of inactive ingredients is from 1 to 50 wt. %, preferably from 10 to 50 wt. % and especially preferably from 20 to 50 wt. %.

Basically, the following methods are available for preparation of the solutions:

Method A: An aqueous suspension is prepared, which contains the pesticide in suspended form and the inactive ingredients of the matrix and optionally the additional components in dissolved form. For this, either the inactive ingredients of the matrix can be dissolved in water first, and the pesticide is then suspended in this solution, or the inactive ingredients of the matrix can be added to an aqueous suspension of the pesticide. The resultant suspension is then heated in a suitable device until the pesticide dissolves.

Method B: An aqueous suspension of the pesticide, which contains the inactive ingredients of the matrix in dissolved form, is prepared as described under method A, and this is heated by mixing with a hot stream of water or steam until the pesticide dissolves.

Method C: As a slight modification of method B, provided the inactive ingredients are thermally stable they can also be dissolved in a stream of hot water and then mixed with a suspension of the pesticide in water.

The following applies, whatever method is selected:

For dispersing the pesticide in water or the aqueous polymer solution, a small grain size is advantageous, because firstly it facilitates dispersion and secondly the dissolution process with heating is quicker. If a coarse pesticide is used, this can also be comminuted or ground in the polymer solution, before the suspension is heated. For example, high-pressure homogenizers, rotor-stator equipment, ball mills or colloid mills can be used for comminution. In principle, however, the pesticide can also, as described, be put in water first, and then the polymer is added.

The aqueous suspension is heated continuously in a suitable device.

Heating can for example take place in any suitable heat exchanger, generally designating, as heat exchangers, devices in which heat is transferred to another medium by means of a heat-transfer agent, in order to achieve heating.

In indirect heat exchange, the heat-transfer agent and the medium to be heated are separated by heat-exchange surfaces. Suitable heat-transfer agents are hot oil, hot steam or superheated water, or even generally hot gases or hot liquids. The heat-transfer agent can be conveyed in countercurrent to the aqueous suspension to be heated. Furthermore, the medium to be heated can also be conveyed continuously through a static heat-transfer agent.

In direct heat exchange, such as takes place according to methods B) or C) according to the invention, the two media are in contact. Therefore superheated water or steam can be considered as the heat-transfer agent for direct heat exchange.

Generally the suspension of active substance can be heated by all methods that provide a very rapid heating rate. Thus, electric, inductive or microwave heating systems are possible.

In order to dissolve the active substance in water, the aqueous suspension is heated to temperatures that are above the boiling point of the mixture at normal pressure. Temperatures of 80° C. to 350° C., preferably 90° C. to 300° C., especially preferably 90° C. to 250° C., can be selected.

To avoid thermal stress of the substances used, regardless of which of the methods described is employed, the residence times during heating to at least 90° C. are kept in the region of seconds. Preferably the residence time of the medium containing the active substance in the device used for heating is less than 180 seconds, especially preferably less than 60 seconds, and quite especially preferably less than 15 seconds. To achieve complete solution of the active substance, generally a minimum residence time of 0.5 second is selected.

Usually the solids content of the solutions is 1 to 70 wt. %, preferably 3 to 60 wt. %, especially preferably 5 to 40 wt. %.

After passing through the device, the hot, pressurized aqueous solution of pesticide, inactive ingredients of the matrix and optionally additional components is led directly to a spraying device. Spraying can be effected by means of nozzles, for which basically single-component or multi-component nozzles are suitable, or by means of rotating disks. Spraying of the preparation in the drying tower is preferably carried out with single-component nozzles at pressures from 10 to 250 bar. However, it is also possible to use multi-component nozzles, in particular two-component nozzles, and the pressure of the spraying gas can be 0.15 to 10 MPa.

The tower inlet temperatures of the drying gas are between 50 and 200° C., preferably between 70 and 180° C. Suitable drying gases are air or inert gases such as nitrogen, argon or helium. The tower outlet temperatures are from 40 to 120° C. The drying gas can be fed into the drying tower in parallel flow or in countercurrent to the liquid droplets in the drying tower, preferably in parallel flow.

As well as simple spray drying, it is also possible to carry out agglomerating spray drying with internal and/or external fluidized bed (e.g. FSD Technology from the company Niro), with the particles that form during spray drying being agglomerated to larger formations.

Generally it is possible to use all drying techniques in which a solution is sprayed, thus including fluidized-bed spray granulation.

If the spray-dried particles display a tendency to be sticky, they can be dusted with a very finely-divided solid. This finely-divided solid is injected into the spraying tower and thus ensures that no sticking or clumping occurs. Suitable substances for dusting are the carriers already defined above.

According to one embodiment, for production of the solid solutions by method A according to the invention, the pesticide is accordingly dispersed in an aqueous solution of the polymer and the suspension is heated in a suitable device to temperatures above 90°, so that the pesticide crystals dissolve. Heating of the polymer solution containing the active substance should be as quick as possible, to reduce the thermal loading of the pesticide. For this, the suspension containing the active substance is led continuously through a suitable device, with the residence times preferably in the range of a few seconds, as already described. This heated, pressurized solution of active substance is then sprayed and dried. The temperature of the spray solution shortly before spraying, i.e. before it is fed into the spraying device, is 80 to 350° C., preferably 90 to 300° C. and especially preferably 90 to 250° C. The pressure of the spray solution is then 0.08 to 20 MPa, preferably 1 to 15 MPa.

According to a preferred embodiment of the invention, the pesticide-containing polymer solution can be pumped through a small-diameter pipeline, which is located in a hot oil bath, at temperatures from 90° C. to 500° C., preferably 110 to 300° C. This makes rapid heat transfer possible. The temperature of the polymer solution containing the active substance is adjusted by varying the oil bath temperature and the flow rate. Directly after it is passed through the pipeline, the hot pressurized solution is sprayed using a spray nozzle and dried with hot drying gas. Evaporation of the water produces sudden cooling and drying of the spray droplets.

Such a procedure is, for example, shown schematically in FIG. 1. The suspension of the active substance in the aqueous solution of the inactive ingredients of the matrix is prepared in a vessel 1 equipped with a stirrer; the suspension is then pumped continuously in a coil through a heat exchanger 2, which is equipped with a heater 2a for heating the heat-transfer agent, and the solution is then sprayed and dried by means of a nozzle 3 in a spraying tower 4, and the resultant particulate solid solution 5 is collected.

According to another embodiment of the invention, the procedure according to method B, presented below, can be selected. This procedure can be recommended especially if the thermal loading of the sparingly-soluble pesticide should be further minimized. The sparingly soluble pesticide is suspended in the polymer solution at room temperature or slightly elevated temperature, at which the pesticide still does not decompose. This suspension is fed to a mixing cell, in which it undergoes turbulent mixing with superheated water or steam. The temperature of the water or steam should be between 90 to 500° C., preferably 110 to 400° C., especially preferably 110° C. to 300° C. Owing to the high temperature of the water or steam and the turbulent mixing, the suspension of the active substance in the polymer solution is heated extremely quickly to temperatures above 90° C. and the active substance goes into solution. Passage through the mixing cell is followed directly by spraying in a spray nozzle and spray drying. The temperature of the solution to be sprayed is controlled by the temperatures of the two liquid streams and their mixing ratio. Higher temperatures of the stream of water or steam and a higher ratio of the stream of water or steam to the pesticide/polymer suspension increase the temperature of the pesticide solution to be sprayed. The residence time in the mixing cell depends on the flow velocity of the two liquid streams and the geometry of the mixing cell. As a rule the suspension of the pesticide in the polymer solution is brought to the desired temperature within fractions of a second. The thermal loading of the pesticide depends moreover on how quickly spray drying is carried out following mixing. The path between mixing cell and spray nozzle should therefore be correspondingly short. Dissolution of the pesticide crystals requires a minimum residence time, which is a function of the dissolution rate specific to the active substance, the temperature of the solution or suspension and the particle size. The total residence time of the pesticide at high temperatures can be set with the flow velocity, the geometry of the mixing cell and the path length to the spray nozzle. As a rule the total residence time is less than 30 seconds, preferably less than 15 seconds and especially preferably less than 5 seconds. With a high dissolution rate of the pesticide, even times of less than 1 second can be achieved.

The ratio of the volume flow rates can be varied from 9:1 to 1:9, for example the ratio of the volume flow rates of pesticide suspension to the stream of hot liquid can be between 9:1 and 1:9, preferably between 7:3 and 3:7.

The geometry of the mixing cell can be of very varied design: from a simple T-piece to very intricate cells with high-turbulence mixing. The angle at which the streams are brought together can be between 5 and 180°. In a particular embodiment, one stream can be injected into the other stream with an injector nozzle.

Other inactive ingredients, for example solubilizers, are as a rule included in the stream containing the active substance, though in principle they can also be incorporated via the hot aqueous phase.

Such a procedure is shown schematically in FIG. 2. A pesticide suspension in a solution of the inactive ingredients of the matrix is prepared in a vessel 6 equipped with a stirrer and is pumped continuously into a mixing cell 8. Water is pumped continuously from a vessel 7 through a heat exchanger 7*a*, which is equipped with a heater 7*b*, and, as superheated water or steam, is also pumped into the mixing cell 8. In mixing cell 8, continuous mixing of the two streams leads to heating and dissolution of the pesticide. The hot solution is then sprayed by means of a nozzle 9 in a spraying tower 10, and the particulate solid solution 11 is collected.

Solid solutions of sparingly soluble pesticides in the form of powders or granules can be obtained by heating an aqueous suspension of the sparingly soluble pesticide in the presence of inactive ingredients of the matrix to temperatures that are above the boiling point at normal pressure, so that the sparingly soluble pesticide dissolves, and the solution of the sparingly soluble pesticide and inactive ingredients of the matrix (spray solution) is then converted to a solid form by spraying and drying, the temperature of the spray solution before it is fed into the spraying device being 80° C. to 350° C. The solid solutions are preferably obtained by heating an aqueous suspension of the sparingly soluble pesticide in the presence of inactive ingredients of the matrix to temperatures that are above the boiling point at normal pressure, so that the sparingly soluble pesticide is dissolved, and the solution of the sparingly soluble pesticide and inactive ingredients of the matrix (spray solution) is then converted to a solid form by spraying and drying, the temperature of the spray solution before it is fed into the spraying device being 80° C. to 350° C.

Preferred embodiments of the methods for the production of solid solutions are as described previously.

The powders or granules according to the invention generally contain, a) 1-50 wt. % pesticide, b) 10-99 wt. % of a water-soluble inactive ingredient of the matrix, c) 0-30 wt. % solubilizers, and d) 0-50 wt. % of other usual inactive ingredients.

Owing to its porosity, the powder produced by the method according to the invention has very good properties for further processing. Usually average grain sizes of 25 to 500 μm are obtained.

The solid solutions of sparingly soluble pesticides according to the invention in the form of powder or granules are used for the production of pesticide-containing formulations.

The powders produced can be used directly (as dusts or wettable powders: WP, SP, SS, WS, DP, DS) or undergo appropriate further processing (to pastes, pellets, wettable powders, dusts (WP, SP, SS, WS, DP, DS) or granules (GR, FG, GG, MG). During further processing, other inactive ingredients, already defined above, can be mixed with the powders produced as above. The technology required for the further processing is known by a person skilled in the art, as the preparations according to the invention can be used analogously to pesticides or pesticide-laden carriers, cf. U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th ed., McGraw-Hill, New York, 1963, p. 8-57 ff., WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th ed., Blackwell Scientific Publications, Oxford, 1989 and Mollet, H., Grubemann, A., Formulation Technology, Wiley VCH Verlag GmbH, Weinheim (Federal Republic of Germany), 2001).

The present invention also relates to a formulation comprising a solid solution produced according to the invention.

All the foregoing embodiments are designated hereinafter as formulations according to the invention.

The advantage of the pesticide formulations produced according to the invention is that high concentrations of active substance are contained as a solid, molecularly disperse solution, so that the solid solution dissolves rapidly in an aqueous medium and the active substance is held in the aqueous medium in the supersaturated range for a long time. As a result, high biological efficacy is achieved.

The present invention also claims methods of controlling the growth of weeds, wherein the weeds, the soils on which the weeds grow, or their seeds are treated with a formulation according to the invention.

The present invention also claims methods for control of insect pests or mites on plants and/or for controlling phytopathogenic fungi, wherein the fungi/insects, their habitat or the plants or soils that are to be protected against attack by fungi or insects, or the plants, the soils on which the plants grow, or their seeds are treated with an agrochemical formulation according to the invention.

Furthermore, the present invention claims methods of treatment of seeds with a pesticide formulation according to the invention and seeds treated with a formulation according to the invention.

For the treatment of seeds, the formulations according to the invention are diluted with water or are used directly. The term "treatment of seeds" comprises all common techniques (seed dressing, seed coating, seed dusting, seed soaking, seed film coating, seed multilayer coating, seed encrusting, seed dripping, and seed pelleting, preferably seed soaking).

The term "seeds" comprises seeds of all kinds, for example grains, seeds, fruits, bulbs, cuttings and similar forms. Here, the term "seeds" preferably describes grains and seeds.

Suitable seeds are cereal seeds, root crop seeds, oil seeds, seeds of vegetables, seeds of herbs and spices, seeds of ornamental plants, e.g. seeds of durum wheat, wheat, barley, oats, rye, maize (animal-feed maize and sweet corn), soya, oil seeds, crucifer, cotton, sunflower, banana, rice, colza, beet, sugar beet, feed beet, eggplant, potatoes, grass, lawn grass, fodder grass, tomatoes, leek, pumpkin, cabbage, iceberg lettuce, peppers, cucumbers, melons, *Brassica* spp. melons, beans, peas, garlic, onions, carrots, tuberous plants such as sugarcane, tobacco, grapes, petunias and geraniums, pansy, touch-me-not, preferably wheat, maize, soya and rice.

The seeds of transgenic plants or plants obtained by conventional breeding methods can also be used as seeds.

Thus, seeds can be used that are tolerant to herbicides, fungicides or insecticides, e.g. to sulfonylureas (e.g. EP-A-0257993, U.S. Pat. No. 5,013,659), imidazolinones (e.g. U.S. Pat. No. 6,222,100, WO0182685, WO0026390, WO9741218, WO9802526, WO9802527, WO 04/106529, WO 05/20673, WO 03/14357, WO 03/13225, WO 03/14356, WO 04/16073), glufosinate-type herbicides (e.g. EP-A-0242236, EP-A-242246) or glyphosate-type herbicides (e.g. WO 92/00377) or herbicides from the classes of the cyclohexadienones/aryloxyphenoxypropionic acids (e.g. U.S. Pat. No. 5,162,602, U.S. Pat. No. 5,290,696, U.S. Pat. No. 5,498,544, U.S. Pat. No. 5,428,001, U.S. Pat. No. 6,069,298, U.S. Pat. No. 6,268,550, U.S. Pat. No. 6,146,867, U.S. Pat. No. 6,222,099, U.S. Pat. No. 6,414,222);
or seeds of transgenic plants, e.g. cotton, which produce *Bacillus thuringiensis* toxin (Bt toxins) and are therefore resistant to certain pests (e.g. EP-A-0142924, EP-A-0193259).

Furthermore, it is also possible to use seeds from plants that have modified properties compared with conventional plants. Examples of this are altered starch synthesis (e.g. WO 92/11376, WO 92/14827, e.g. WO 91/19806) or fatty acid compositions (e.g. WO 91/13972).

Controlling the growth of weeds means the control/destruction of plants that are growing in places where they are undesirable, e.g. of
dicotyledonous plants of the species: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutylon, Emex, Datura, Viola, Galeopsis, Papaver, Centaurea, Trifolium, Ranunculus, Taraxacum;*
monocotyledonous plants of the species: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus, Apera.*

The term insect or mite pests describes, but is not restricted to, the following genera:

Lepidoptera, for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyla pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;*

Beetles (Coleoptera) for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Cheatocnema tibialis, Conoderus vespertinus, Cryoceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;*

Diptera, for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;*

Thysanoptera, for example *Frankliniella fusca, Frankliniella occidentalis, Frankliniella tritici, Scirtothrips citri, Thrips oryzae, Thrips palmi* and *Thrips tabaci;*

Hymenoptera, for example *Athalia rosae, Atta cephalotes, Atta sexdens, Atta texana, Hoplocampa minuta, Hoplocampa testudinea, Monomorium pharaonis, Solenopsis geminata* and *Solenopsis invicta;*

Heteroptera, for example *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor;*

Homoptera, for example *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphum rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantliund,* and *Viteus vitifolii;*

Termites (Isoptera), e.g. *Calotermes flavicollis, Leucotermes flavipes, Reticulitermes lucifugus* and *Termes natalensis;*

Orthoptera, e.g. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus;*

Arachnoidea, for example Acarina, e.g. from the families Argasidae, Ixodidae and Sarcoptidae, e.g. *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and Eriophyidae spp. e.g. *Aculus schlechtendali, Phyllocoptrata oleivora* and *Eriophyes sheldoni*; Tarsonemidae spp. e.g. *Phytonemus pallidus* and *Polyphagotarsonemus latus*; Tenuipalpidae spp. e.g. *Brevipalpus phoenicis*; Tetranychidae spp. e.g. *Tetranychus cinnabarinus, Tetranychus kanzawai, Tetranychus pacificus, Tetranychus telarius* and *Tetranychus urticae, Panonychus ulmi, Panonychus citri,* and *Oligonychus pratensis;*

Nematodes, especially nematodes parasitic on plants, e.g. plant root knot nematodes, *Meloidogyne hapla, Meloidogyne incognita, Meloidogyne javanica,* and other *Meloidogyne* species; cyst-forming nematodes, *Globodera rostochiensis* and other *Globodera* species; *Heterodera avenae, Heterodera glycines, Heterodera schachtii, Heterodera trifolii,* and other *Heterodera* species; seed gall nematodes, *Anguina* species; stem and foliar nematodes, *Aphelenchoides* species; sting nematodes, *Belonolaimus longicaudatus* and other *Belonolaimus* species; pine nematodes, *Bursaphelenchus xylophilus* and other *Bursaphelenchus* species; ring nematodes, *Criconema* species, *Criconemella* species, *Criconemoides* species, *Mesocriconema* species; stem and bulb nematodes, *Ditylenchus destructor, Ditylenchus dipsaci* and other *Ditylenchus* species; awl nematodes, *Dolichodorus* species; spiral nematodes, *Heliocotylenchus multicinetus* and other *Helicotylenchus* species; sheath and sheathoid nematodes, *Hemicycliophora* species and *Hemicriconemoides* species; *Hirshmanniella* species; lance nematodes, *Hoploaimus* species; false rootknot nematodes, *Nacobbus* species; needle nematodes, *Longidorus elongatus* and other *Longidorus* species; lesion nematodes, *Pratylenchus neglectus, Pratylenchus penetrans, Pratylenchus curvitatus, Pratylenchus goodeyi* and other *Pratylenchus* species; burrowing nematodes, *Radopholus similis* and other *Radopholus* species; reniform nematodes, *Rotylenchus robustus* and other *Rotylenchus* species; *Scutellonema* species; stubby root nematodes, *Trichodorus primitivus* and other *Trichodorus* species, *Paratrichodorus* species; stunt nematodes, *Tylenchorhynchus claytoni, Tylenchorhynchus dubius* and other *Tylenchorhynchus* species; citrus nematodes, *Tylenchulus* species; dagger nematodes, *Xiphinema* species;

and rice pathogens, e.g. rice water weevil (*Lissorhoptrus oryzaphilus*), rice stem borer (*Chilo suppresalis*), rice leaf roller, rice leaf beetle, rice leaf miner (*Agromyca oryza*), leafhoppers (*Nephotettix* spp.; especially smaller brown leafhopper, green rice leafhopper), planthoppers (Delphacidae; especially white backed planthopper, brown rice planthopper), stinkbugs;

The term phytopathogenic fungi describes, but is not restricted to, the following species:

*Blumeria graminis* (true mildew) on cereals, *Erysiphe cichoracearum* and *Sphaerotheca fuliginea* on pumpkin plants, *Podosphaera leucotricha* on apples, *Uncinula necator* on vines, *Puccinia* species on cereals, *Rhizoctonia* species on cotton, rice and lawns, *Ustilago* species on cereals and sugarcane, *Venturia inequalis* on apples, *Bipolaris* and *Drechslera* species on cereals, rice and lawns, *Septoria nodorum* on wheat, *Botrytis cinerea* on strawberries, vegetables, ornamental plants and vines, *Mycosphaerella* species on bananas, groundnuts and cereals, *Pseudocercosporella herpotrichoides* on wheat and barley, *Pyricularia oryzae* on rice, *Phytophthora infestans* on potatoes and tomatoes, *Pseudoperonospora* species on pumpkin plants and hops, *Plasmopara viticola* on vines, *Alternaria* species on vegetables and fruit and *Fusarium* and *Verticillium* species, *Bipolaris* and *Drechslera* species and *Pyricularia oryzae, Corticium sasakii* (syn. *Rhizoctonia solani*) and *Cochliobolus miyabeanus* on rice plants and possibly on their seeds, *Paecilomyces variotii* on materials such as wood.

EXAMPLES

Polymers used
  Luviskol® K30: pulverulent polyvinylpyrrolidone with K value of 29-33 (at 1 wt. % in water), commercially available from BASF Aktiengesellschaft.
  Luviskol® VA64: pulverulent copolymer of vinylpyrrolidone and vinylacetate in the ratio 6/4 with K value of 26-34 (at 1 wt. % in ethanol), commercially available from BASF Aktiengesellschaft.

Block VPNAc: block copolymer of polyvinylpyrrolidone and polyvinylacetate in the molar ratio 6/4 (Mn=13900, polydispersity index 1.9, determined by gel permeation chromatography and calculated as PDI=$M_w$:$M_n$).

AMPS/PEA/BA: copolymer of 2-acrylamido-2-methyl-1-propanesulfonic acid/cophenoxyethyl acrylate/co-n-butyl acrylate in the weight ratio 17/33/50, produced as in Example 1 of WO2005/046328.

In the following examples, the heat exchanger used was a thin-walled coil with a diameter of 10 mm, in an oil bath at a temperature of 150° C.

Example 1

Solid Solution of Pyraclostrobin 35.0 kg Luviskol® K30 was dissolved in 91.0 kg demineralized water. 10.5 kg of finely ground pyraclostrobin was suspended in this polymer solution, while stirring vigorously. In addition, 1.8 kg Wettol® NT1 (from BASF; alkyl naphthalenesulfonic acid condensate, sodium salt) was added to the aqueous suspension. Short-term high temperature heating was carried out by pumping the aqueous suspension through a heat exchanger, raising the temperature of the solution to 135° C. The flow rate, which was generated with a high-pressure pump, was 700 to 800 ml/min, at a pressure of 9 MPa. The hot solution obtained was sprayed and dried in a spray dryer using a single component nozzle with 0.7 mm diameter at a pressure of 90 bar. With an inlet air temperature of 150° C., the outlet air temperature was 97° C. A dry powder with excellent flow properties was obtained.

Examples 2-9

Solid Solution of Pyraclostrobin and Epoxiconazole or Meconazole 35.0 kg Luviskol® K30 was dissolved in 91.0 kg demineralized water. 6.1 kg of finely ground pyraclostrobin and 4.4 kg of finely ground epoxiconazole (pesticide 2) were suspended in this polymer solution, while stirring vigorously. In addition, 1.8 kg Wettol® NT1 was added to the solution. Short-term high-temperature heating was carried out by pumping the solution through a heat exchanger, raising the temperature of the solution to 133° C. The flow rate, which was generated with a high-pressure pump, was 700 to 800 ml/min, at a pressure of 9 mPa. The hot solution obtained was sprayed and dried in a spray dryer using a single-component nozzle with 0.7 mm diameter at a pressure of 90 bar. At an inlet air temperature of 145° C., the outlet air temperature was 95° C. A dry powder with excellent flow properties was obtained.

Examples 3 to 9 were carried out as in Example 3. As pesticide 2, epoxiconazole was partially replaced with metconazole (see Table 1, column "Pesticide 2"). Various other polymers were used instead of Wettol® NT1 (see Table 1, column "Polymer"). The amounts used were not changed.

TABLE 1

| Example | Pesticide 2 | Polymer |
| --- | --- | --- |
| 3 | Epoxiconazole | Luviskol ® VA64 |
| 4 | Epoxiconazole | Block VP/Vac |
| 5 | Epoxiconazole | AMPS/PEA/BA |
| 6 | Metconazole | Luviskol ® K30 |
| 7 | Metconazole | Luviskol ® VA64 |
| 8 | Metconazole | Block VP/Vac |
| 9 | Metconazole | AMPS/PEA/BA |

The invention claimed is:

1. A method for the production of pulverulent or granulated solid solution of a sparingly soluble pesticide, in which the sparingly soluble pesticide is molecularly dispersed in a matrix of inactive ingredients, comprising
preparing a hot, pressurized aqueous solution of the pesticide and of the inactive ingredients of the matrix by heating an aqueous suspension of the sparingly soluble pesticide in the presence of the inactive ingredients of the matrix to temperatures that are above the boiling point at normal pressure and the sparingly soluble pesticide is dissolved, the temperatures during heating being in the range from 90° C. to 300° C., and
converting the hot, pressurized aqueous solution of the sparingly soluble pesticide and of the inactive ingredients of the matrix to a solid form by spraying and drying, the temperature of the hot, pressurized aqueous solution before being fed into a spraying device being between 90° C. to 300° C., and the pressure of the aqueous solution before feed into the spraying device being from 1 to 15 MPa,
where the aqueous suspension of the sparingly soluble pesticide in the presence of the inactive ingredients of the matrix is heated continuously in a devices such that the residence time of the solution containing the active substance at temperatures above 90° C. is less than 180 seconds and where the solution is led directly to a spraying device,
where the pesticide is selected from the group consisting of insecticides, fungicides, herbicides and safeners and where the solubility of the pesticide at 20° C. is less than 1% by weight in water, 0.1 molar aqueous hydrochloric acid, aqueous phosphate buffer at pH 7.2, and 0.9 wt. % aqueous sodium chloride,
and where the sparingly soluble pesticide molecularly dispersed in the matrix of inactive ingredients has a crystalline fraction less than 3 wt. %.

2. The method of claim 1, wherein the concentration of the sparingly soluble pesticide in the matrix of inactive ingredients is between 1 and 50 wt. %.

3. The method of claim 1, wherein the solution contains an adsorbent.

4. The method of claim 1, wherein the aqueous suspension of the pesticide is heated by mixing with a hot stream of liquid or a hot stream of steam.

5. The method of claim 4, wherein the ratio of the suspension of the pesticide to the hot liquid stream is between 9:1 and 1:9.

6. The method of claim 1, wherein methods of spray drying or fluidized-bed spray granulation are used for drying.

7. The method of claim 6, wherein an adsorbent or dusting agent is injected into a spraying tower during spray drying.

8. The method of claim 1, where the pesticide is a fungicide selected from the group consisting of triazoles, strobilurins and boscalid.

9. The method of claim 1, where the pesticide is a fungicide selected from the group consisting of epoxiconazole, metconazole, pyraclostrobin, kresoxim-methyl, 5-chloro-7-(4-methylpiperidin-1-yl)-6-(2,4,6-trifluorophenyl)-[1,2,4]triazolo[1,5-a]pyrimidine and boscalid.

10. The method of claim 1, where the pesticide is an insecticide selected from the group consisting of metaflumizone, fipronil and alpha-cypermethrin.

11. The method of claim 1, where the matrix forming inactive ingredients comprise a water soluble polymer, selected from the group consisting of polyvinylpyrrolidone, vinylpyrrolidone-vinylacetate copolymers, polyvinylcaprolactams, polyvinylformamide, polyvinylacetamide, polyacrylates, polymethacrylates, polyacrylamides, polyethylene-imines, polyvinylamines, hydroxyalkylcelluloses, alkylhydroxyalkylcelluloses, carboxyalkylcelluloses, alkylhydroxyalkylcellulose-acetate-succinates, alkyl-hydroxyalkylcellulose-acetatephthalates, alkylhydroxyalkylcellulose-phthalates, celluloseacetate-phthalates, starches, hydroxy alkyl starches, carboxy alkyl starches, modified starch, octenylsuccinate-starches, dextrans, polyoxyethylene-polyoxypropylene block copolymers, polyethylene oxides, polypropylene oxides, and polyamino acids.

12. The method of claim 1, where the matrix forming inactive ingredients comprise a water soluble polymer, selected from the group consisting of polyvinylpyrrolidone and vinylpyrrolidone-vinylacetate copolymers.

* * * * *